(12) United States Patent
Oepen

(10) Patent No.: US 8,617,184 B2
(45) Date of Patent: Dec. 31, 2013

(54) VESSEL CLOSURE SYSTEM

(75) Inventor: Randolf Von Oepen, Los Altos Hills, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 189 days.

(21) Appl. No.: 13/028,041

(22) Filed: Feb. 15, 2011

(65) Prior Publication Data

US 2012/0209317 A1  Aug. 16, 2012

(51) Int. Cl.
*A61B 17/10* (2006.01)

(52) U.S. Cl.
USPC .................. 606/142; 606/213; 227/175.1

(58) Field of Classification Search
None
See application file for complete search history.

(56) References Cited

U.S. PATENT DOCUMENTS

| 287,046 | A | 10/1883 | Norton |
|---|---|---|---|
| 1,088,393 | A | 2/1914 | Backus |
| 1,242,139 | A | 10/1917 | Callahan |
| 1,331,401 | A | 2/1920 | Summers |
| 1,480,935 | A | 1/1924 | Gleason |
| 1,596,004 | A | 8/1926 | De Bengoa |
| 2,087,074 | A | 7/1937 | Tucker |
| 2,316,297 | A | 4/1943 | Southerland et al. |
| 2,453,227 | A | 11/1948 | James |
| 2,684,070 | A | 7/1954 | Kelsey |
| 2,944,311 | A | 7/1960 | Schneckenberger |
| 2,951,482 | A | 9/1960 | Sullivan |
| 2,969,887 | A | 1/1961 | Darmstadt et al. |
| 3,015,403 | A | 1/1962 | Fuller |
| 3,142,878 | A | 8/1964 | Santora |
| 3,348,595 | A | 10/1967 | Stevens, Jr. |
| 3,357,070 | A | 12/1967 | Sloan |
| 3,482,428 | A | 12/1969 | Kapitanov et al. |
| 3,586,002 | A | 6/1971 | Wood et al. |
| 3,604,425 | A | 9/1971 | Le Roy |
| 3,618,447 | A | 11/1971 | Goins |
| 3,677,243 | A | 7/1972 | Nerz |
| 3,682,180 | A | 8/1972 | McFarlane |
| 3,757,629 | A | 9/1973 | Schneider |

(Continued)

FOREIGN PATENT DOCUMENTS

| CA | 2 339 060 | 2/2000 |
|---|---|---|
| DE | 197 11 288 | 10/1998 |

(Continued)

OTHER PUBLICATIONS

U.S. Appl. No. 13/490,143, Mail Date Jan. 4, 2013, Office Action.

(Continued)

*Primary Examiner* — Melanie Tyson
*Assistant Examiner* — Todd J Scherbel
(74) *Attorney, Agent, or Firm* — Workman Nydegger; Randy Shen

(57) ABSTRACT

A power driven vessel closure device is configured for closing a hole in a wall of a body lumen. The vessel closure device can include a power operated drive system and a closure element delivery system. The closure element delivery system can be removably, operably, couplable with the power operated drive system. That is, the closure element system can be directly or indirectly attached to and removed from the power operated drive system, or components thereof. The operation of the power operated drive system can operate the closure element delivery system so as to move the closure element within the vessel closure device and deploy the closure element to close the hole.

12 Claims, 13 Drawing Sheets

(56) References Cited

U.S. PATENT DOCUMENTS

| | | | |
|---|---|---|---|
| 3,805,337 A | 4/1974 | Branstetter |
| 3,856,016 A | 12/1974 | Davis |
| 3,874,388 A | 4/1975 | King et al. |
| 3,944,114 A | 3/1976 | Coppens |
| 4,014,492 A | 3/1977 | Rothfuss |
| 4,064,881 A | 12/1977 | Meredith |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,207,870 A | 6/1980 | Eldridge |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,278,091 A | 7/1981 | Borzone |
| 4,317,445 A | 3/1982 | Robinson |
| 4,318,401 A | 3/1982 | Zimmerman |
| 4,345,606 A | 8/1982 | Littleford |
| 4,359,052 A * | 11/1982 | Staub ............................ 606/30 |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,695 A | 6/1985 | Braun et al. |
| 4,525,157 A | 6/1985 | Valaincourt |
| 4,586,503 A | 5/1986 | Kirsch et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,665,906 A | 5/1987 | Jervis |
| 4,687,469 A | 8/1987 | Osypka |
| 4,697,312 A | 10/1987 | Freyer |
| 4,724,840 A | 2/1988 | McVay et al. |
| 4,738,658 A | 4/1988 | Magro et al. |
| 4,744,364 A | 5/1988 | Kensey |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,886,067 A | 12/1989 | Palermo |
| 4,887,601 A | 12/1989 | Richards |
| 4,917,087 A | 4/1990 | Walsh et al. |
| 4,934,364 A | 6/1990 | Green |
| 4,950,258 A | 8/1990 | Kawai et al. |
| 4,961,729 A | 10/1990 | Vaillancourt |
| 4,967,949 A | 11/1990 | Sandhaus |
| 4,997,436 A | 3/1991 | Oberlander |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,035,692 A | 7/1991 | Lyon et al. |
| 5,053,008 A | 10/1991 | Bajaj |
| 5,061,274 A | 10/1991 | Kensey |
| 5,100,418 A | 3/1992 | Yoon et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,122,122 A | 6/1992 | Allgood |
| 5,131,379 A | 7/1992 | Sewell, Jr. |
| 5,147,381 A | 9/1992 | Heimerl et al. |
| 5,156,609 A | 10/1992 | Nakao et al. |
| 5,167,634 A | 12/1992 | Corrigan, Jr. et al. |
| 5,167,643 A | 12/1992 | Lynn |
| 5,171,249 A | 12/1992 | Stefanchik et al. |
| 5,176,648 A | 1/1993 | Holmes et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,207,697 A * | 5/1993 | Carusillo et al. ............... 606/167 |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,275,616 A | 1/1994 | Fowler |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,184 A | 4/1994 | Hathaway et al. |
| 5,306,254 A | 4/1994 | Nash et al. |
| 5,318,542 A | 6/1994 | Hirsch et al. |
| 5,320,639 A | 6/1994 | Rudnick |
| 5,327,908 A | 7/1994 | Gerry |
| 5,334,216 A | 8/1994 | Vidal et al. |
| 5,334,217 A | 8/1994 | Das |
| 5,350,399 A | 9/1994 | Erlebacher et al. |
| 5,352,229 A | 10/1994 | Goble et al. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| RE34,866 E | 2/1995 | Kensey et al. |
| 5,392,978 A | 2/1995 | Valez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,423,857 A | 6/1995 | Rosenman et al. |
| 5,425,489 A | 6/1995 | Shichman et al. |
| 5,431,639 A | 7/1995 | Shaw |
| 5,433,721 A * | 7/1995 | Hooven et al. ................. 606/143 |
| 5,437,631 A | 8/1995 | Janzen |
| 5,439,479 A | 8/1995 | Shichman et al. |
| 5,443,481 A | 8/1995 | Lee |
| 5,445,167 A | 8/1995 | Yoon et al. |
| 5,451,235 A | 9/1995 | Lock et al. |
| 5,456,400 A | 10/1995 | Shichman et al. |
| 5,470,010 A | 11/1995 | Rothfuss et al. |
| 5,474,557 A | 12/1995 | Mai |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,716 A | 7/1996 | Hlavacek |
| 5,544,802 A | 8/1996 | Crainich |
| 5,560,532 A | 10/1996 | DeFonzo et al. |
| 5,591,205 A | 1/1997 | Fowler |
| 5,593,412 A | 1/1997 | Martinez et al. |
| 5,601,602 A | 2/1997 | Fowler |
| 5,620,452 A | 4/1997 | Yoon |
| 5,620,461 A | 4/1997 | Muijs et al. |
| 5,634,936 A | 6/1997 | Linden et al. |

(56) References Cited

U.S. PATENT DOCUMENTS

| | | |
|---|---|---|
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,700,273 A | 12/1997 | Buelna et al. |
| 5,716,375 A | 2/1998 | Fowler |
| 5,725,554 A | 3/1998 | Simon et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,830,125 A | 11/1998 | Scribner et al. |
| 5,845,657 A | 12/1998 | Carberry et al. |
| 5,853,421 A | 12/1998 | Leschinsky et al. |
| 5,855,312 A | 1/1999 | Toledano |
| 5,861,005 A | 1/1999 | Kontos |
| 5,868,755 A | 2/1999 | Kanner et al. |
| 5,871,474 A | 2/1999 | Hermann et al. |
| 5,871,501 A | 2/1999 | Leschinsky et al. |
| 5,871,525 A | 2/1999 | Edwards et al. |
| 5,879,366 A | 3/1999 | Shaw et al. |
| 5,902,310 A | 5/1999 | Foerster et al. |
| 5,910,155 A | 6/1999 | Ratcliff et al. |
| 5,919,207 A | 7/1999 | Taheri |
| 5,922,009 A | 7/1999 | Epstein et al. |
| 5,935,147 A | 8/1999 | Kensey et al. |
| 5,941,890 A | 8/1999 | Voegele et al. |
| 5,951,518 A | 9/1999 | Licata et al. |
| 5,951,589 A | 9/1999 | Epstein et al. |
| 5,957,940 A | 9/1999 | Tanner et al. |
| 5,964,782 A | 10/1999 | Lafontaine et al. |
| 5,984,934 A | 11/1999 | Ashby et al. |
| 5,984,949 A | 11/1999 | Levin |
| 5,993,468 A | 11/1999 | Rygaard |
| 5,993,476 A | 11/1999 | Groiso |
| 6,004,341 A | 12/1999 | Zhu et al. |
| 6,007,563 A | 12/1999 | Nash et al. |
| 6,013,084 A | 1/2000 | Ken et al. |
| 6,022,372 A | 2/2000 | Kontos |
| 6,024,756 A | 2/2000 | Huebsch et al. |
| 6,030,364 A | 2/2000 | Durgin et al. |
| 6,033,427 A | 3/2000 | Lee |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,063,085 A | 5/2000 | Tay et al. |
| 6,063,114 A | 5/2000 | Nash et al. |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,612 A | 9/2000 | Swanson et al. |
| 6,117,125 A | 9/2000 | Rothbarth et al. |
| 6,117,148 A | 9/2000 | Ravo |
| 6,117,159 A | 9/2000 | Huebsch et al. |
| 6,120,524 A | 9/2000 | Taheri |
| 6,146,385 A | 11/2000 | Torrie et al. |
| 6,149,660 A | 11/2000 | Laufer et al. |
| 6,149,667 A | 11/2000 | Hovland et al. |
| 6,152,937 A | 11/2000 | Peterson et al. |
| 6,161,263 A | 12/2000 | Anderson |
| 6,174,322 B1 | 1/2001 | Schneidt |
| 6,197,042 B1 | 3/2001 | Ginn et al. |
| 6,273,903 B1 | 8/2001 | Wilk |
| 6,277,140 B2 | 8/2001 | Ginn et al. |
| 6,287,322 B1 | 9/2001 | Zhu et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,322,580 B1 | 11/2001 | Kanner |
| 6,334,865 B1 | 1/2002 | Redmond et al. |
| 6,348,064 B1 | 2/2002 | Kanner |
| 6,355,052 B1 | 3/2002 | Neuss et al. |
| 6,383,208 B1 | 5/2002 | Sancoff et al. |
| 6,391,048 B1 | 5/2002 | Ginn et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,428,548 B1 | 8/2002 | Durgin et al. |
| 6,443,158 B1 | 9/2002 | Lafontaine et al. |
| 6,447,540 B1 | 9/2002 | Fontaine et al. |
| 6,450,391 B1 | 9/2002 | Kayan et al. |
| 6,461,364 B1 | 10/2002 | Ginn et al. |
| 6,488,692 B1 | 12/2002 | Spence et al. |
| 6,506,210 B1 | 1/2003 | Kanner |
| 6,514,280 B1 | 2/2003 | Gilson |
| 6,517,569 B2 | 2/2003 | Mikus et al. |
| 6,533,762 B2 | 3/2003 | Kanner et al. |
| 6,547,806 B1 | 4/2003 | Ding |
| 6,569,173 B1 | 5/2003 | Blatter et al. |
| 6,578,585 B1 | 6/2003 | Stachowski et al. |
| 6,582,452 B2 | 6/2003 | Coleman et al. |
| 6,602,263 B1 | 8/2003 | Swanson et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,623,510 B2 | 9/2003 | Carley et al. |
| 6,626,918 B1 | 9/2003 | Ginn et al. |
| 6,626,920 B2 | 9/2003 | Whayne |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,669,714 B2 | 12/2003 | Coleman et al. |
| 6,679,904 B2 | 1/2004 | Gleeson et al. |
| 6,689,147 B1 | 2/2004 | Koster, Jr. |
| 6,695,867 B2 | 2/2004 | Ginn et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,846,319 B2 | 1/2005 | Ginn et al. |

(56) References Cited

U.S. PATENT DOCUMENTS

| | | |
|---|---|---|
| 6,849,078 B2 | 2/2005 | Durgin et al. |
| 6,904,647 B2 | 6/2005 | Byers, Jr. |
| 6,926,731 B2 | 8/2005 | Coleman et al. |
| 6,929,634 B2 | 8/2005 | Dorros et al. |
| 6,942,674 B2 | 9/2005 | Belef et al. |
| 6,984,238 B2 | 1/2006 | Gifford, III et al. |
| 6,989,003 B2 | 1/2006 | Wing et al. |
| 7,001,398 B2 | 2/2006 | Carley et al. |
| 7,025,776 B1 | 4/2006 | Houser et al. |
| 7,108,709 B2 | 9/2006 | Cummins |
| 7,111,768 B2 | 9/2006 | Cummins et al. |
| 7,144,411 B2 | 12/2006 | Ginn et al. |
| 7,163,551 B2 | 1/2007 | Anthony et al. |
| 7,169,164 B2 | 1/2007 | Borillo et al. |
| 7,211,101 B2 | 5/2007 | Carley et al. |
| 7,229,452 B2 * | 6/2007 | Kayan .......................... 606/142 |
| D566,272 S | 4/2008 | Walberg et al. |
| 7,431,729 B2 | 10/2008 | Chanduszko |
| 7,582,104 B2 | 9/2009 | Corcoran et al. |
| 7,645,285 B2 | 1/2010 | Cosgrove et al. |
| 7,799,042 B2 | 9/2010 | Williamson, IV et al. |
| 7,806,904 B2 | 10/2010 | Carley et al. |
| 7,819,895 B2 | 10/2010 | Ginn et al. |
| 7,842,068 B2 | 11/2010 | Ginn |
| 7,854,810 B2 | 12/2010 | Carley et al. |
| 7,857,828 B2 | 12/2010 | Jabba et al. |
| 7,867,249 B2 | 1/2011 | Palermo et al. |
| 7,879,071 B2 | 2/2011 | Carley et al. |
| 7,887,555 B2 | 2/2011 | Carley et al. |
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0049427 A1 | 4/2002 | Wiener et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0107542 A1 | 8/2002 | Kanner et al. |
| 2002/0151921 A1 | 10/2002 | Kanner et al. |
| 2003/0004543 A1 | 1/2003 | Gleeson et al. |
| 2003/0009180 A1 | 1/2003 | Hinchliffe et al. |
| 2003/0032981 A1 | 2/2003 | Kanner et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092973 A1 | 5/2004 | Chanduszko et al. |
| 2004/0093024 A1 | 5/2004 | Lousararian et al. |
| 2004/0143291 A1 | 7/2004 | Corcoran et al. |
| 2004/0167570 A1 | 8/2004 | Pantages |
| 2004/0254591 A1 | 12/2004 | Kanner et al. |
| 2004/0267312 A1 | 12/2004 | Kanner et al. |
| 2005/0090859 A1 | 4/2005 | Ravlkumar |
| 2005/0119695 A1 | 6/2005 | Carley et al. |
| 2005/0165357 A1 | 7/2005 | McGuckin et al. |
| 2005/0216057 A1 | 9/2005 | Coleman et al. |
| 2005/0228443 A1 | 10/2005 | Yassinzadeh |
| 2005/0273136 A1 | 12/2005 | Belef et al. |
| 2005/0274768 A1 | 12/2005 | Cummins et al. |
| 2006/0058844 A1 | 3/2006 | White et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0287674 A1 | 12/2006 | Ginn et al. |
| 2007/0010853 A1 | 1/2007 | Ginn et al. |
| 2007/0027525 A1 | 2/2007 | Ben-Muvhar |
| 2007/0060951 A1 | 3/2007 | Shannon |
| 2007/0083231 A1 | 4/2007 | Lee |
| 2007/0123936 A1 | 5/2007 | Goldin et al. |
| 2007/0213747 A1 | 9/2007 | Monassevitch et al. |
| 2007/0270904 A1 | 11/2007 | Ginn |
| 2007/0276416 A1 | 11/2007 | Ginn et al. |
| 2007/0282352 A1 | 12/2007 | Carley et al. |
| 2008/0004636 A1 | 1/2008 | Walberg et al. |
| 2008/0065152 A1 | 3/2008 | Carley |
| 2008/0210737 A1 | 9/2008 | Ginn et al. |
| 2008/0221616 A1 | 9/2008 | Ginn et al. |
| 2008/0287988 A1 | 11/2008 | Smith et al. |
| 2008/0312666 A1 | 12/2008 | Ellingwood et al. |
| 2008/0312686 A1 | 12/2008 | Ellingwood |
| 2009/0105728 A1 | 4/2009 | Noda et al. |
| 2009/0137900 A1 | 5/2009 | Bonner et al. |
| 2010/0217132 A1 | 8/2010 | Ellingwood et al. |
| 2010/0249828 A1 | 9/2010 | Mavani et al. |
| 2011/0066163 A1 | 3/2011 | Cho et al. |
| 2011/0071565 A1 | 3/2011 | Ginn |
| 2011/0106148 A1 | 5/2011 | Ginn et al. |
| 2012/0035630 A1 | 2/2012 | Roorda |
| 2012/0245603 A1 | 9/2012 | Voss |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |

FOREIGN PATENT DOCUMENTS

| | | |
|---|---|---|
| DE | 29723736 U1 | 4/1999 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| FR | 2 443 238 | 7/1980 |
| FR | 2 722 975 | 2/1996 |
| GB | 1 358 466 | 7/1974 |
| GB | 2 075 144 | 11/1981 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| NL | 9302140 | 7/1995 |
| WO | WO 96/24291 | 8/1996 |
| WO | WO 97/07741 | 3/1997 |
| WO | WO 97/20505 | 6/1997 |
| WO | WO 98/06448 | 2/1998 |
| WO | WO 98/17179 | 4/1998 |
| WO | WO 98/24374 | 6/1998 |
| WO | WO 98/25508 | 6/1998 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |

(56) References Cited

FOREIGN PATENT DOCUMENTS

| | | |
|---|---|---|
| WO | WO 00/07640 | 2/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/35832 | 5/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/45593 | 6/2002 |
| WO | WO 02/45594 | 6/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/101310 | 12/2003 |
| WO | WO 2004/004578 | 1/2004 |
| WO | WO 2004/060169 | 7/2004 |
| WO | WO 2004/069054 | 8/2004 |
| WO | WO 2005/082256 | 9/2005 |
| WO | WO 2005/115521 | 12/2005 |
| WO | WO 2006/083889 | 8/2006 |
| WO | WO 2007/005585 | 1/2007 |
| WO | WO 2008/031102 | 3/2008 |
| ZA | 200100527 | 1/2001 |

OTHER PUBLICATIONS

U.S. Appl. No. 13/615,547, Mail Date Jan. 18, 2013, Office Action.
U.S. Appl. No. 11/675,462, Mail Date Dec. 22, 2011, Notice of Allowance.
U.S. Appl. No. 12/393,877, Mail Date Dec. 13, 2011, Office Action.
U.S. Appl. No. 12/684,562, Mail Date Dec. 28, 2011, Office Action.
U.S. Appl. No. 12/897,358, Mail Date Jan. 12, 2012, Notice of Allowance.
U.S. Appl. No. 12/941,809, Mail Date Dec. 13, 2011, Office Action.
U.S. Appl. No. 12/955,859, Mail Date Dec. 15, 2011, Office Action.
U.S. Appl. No. 12/961,331, Mail Date Feb. 1, 2013, Office Action.
U.S. Appl. No. 13/153,594, Mail Date Jan. 29, 2013, Office Action.
U.S. Appl. No. 12/941,809, Mail Date Jan. 30, 2012, Office Action.
U.S. Appl. No. 12/143,020, Mail Date Feb. 23, 2012, Notice of Allowance.
U.S. Appl. No. 12/973,204, Mail Date Mar. 7, 2012, Notice of Allowance.
U.S. Appl. No. 12/987,792, Mail Date Mar. 13, 2012, Office Action.
U.S. Appl. No. 13/308,227, filed Nov. 30, 2011, Yibarren.
U.S. Appl. No. 09/866,551, filed May 25, 2001, Ginn.
U.S. Appl. No. 12/113,092, filed Apr. 30, 2008, Ginn et al.
U.S. Appl. No. 12/961,331, filed Dec. 6, 2010, Voss.
U.S. Appl. No. 12/973,204, filed Dec. 26, 2010, Jabba et al.
U.S. Appl. No. 12/987,792, filed Jan. 10, 2011, Palermo et al.
U.S. Appl. No. 13/039,087, filed Mar. 2, 2011, Palermo et al.
U.S. Appl. No. 13/112,618, filed May 20, 2011, Gianotti et al.
U.S. Appl. No. 13/112,631, filed May 20, 2011, Voss.
U.S. Appl. No. 60/696,069, filed Jul. 1, 2005, Pantages et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
Database WPI; Section PQ, Week 200120; Derwent Publications Ltd., London GB; AN 2001-203165; XP002199926 & ZA 200 100 528 A (Anthony T), Feb. 28, 2001 abstract.
U.S. Appl. No. 09/478,179, Mail Date Nov. 6, 2000, Notice of Allowance.
U.S. Appl. No. 09/546,998, Mail Date May 6, 2002, Notice of Allowance.
U.S. Appl. No. 09/610,238, Mail Date Mar. 26, 2001, Notice of Allowance.
U.S. Appl. No. 09/610,238, Mail Date Sep. 5, 2001, Office Action.
U.S. Appl. No. 09/610,238, Mail Date Feb. 11, 2002, Notice of Allowance.
U.S. Appl. No. 09/680,837, Mail Date Jul. 9, 2002, Office Action.
U.S. Appl. No. 09/680,837, Mail Date Nov. 6, 2002, Office Action.
U.S. Appl. No. 09/680,837, Mail Date Mar. 25, 2003, Office Action.
U.S. Appl. No. 09/680,837, Mail Date Jun. 16, 2003, Notice of Allowance.
U.S. Appl. No. 09/732,835, Mail Date Sep. 11, 2003, Office Action.
U.S. Appl. No. 09/732,835, Mail Date Feb. 9, 2004, Office Action.
U.S. Appl. No. 09/732,835, Mail Date Mar. 17, 2004, Notice of Allowance.
U.S. Appl. No. 09/764,813, Mail Date Mar. 26, 2001, Office Action.
U.S. Appl. No. 09/764,813, Mail Date Jun. 4, 2001, Notice of Allowance.
U.S. Appl. No. 09/933,299, Mail Date Feb. 26, 2003, Office Action.
U.S. Appl. No. 09/933,299, Mail Date Jun. 16, 2003, Notice of Allowance.
U.S. Appl. No. 10/006,400, Mail Date Aug. 27, 2004, Office Action.
U.S. Appl. No. 10/006,400, Mail Date Feb. 23, 2005, Office Action.
U.S. Appl. No. 10/006,400, Mail Date Apr. 11, 2005, Office Action.
U.S. Appl. No. 10/006,400, Mail Date Jul. 27, 2005, Office Action.
U.S. Appl. No. 10/006,400, Mail Date Mar. 6, 2006, Office Action.
U.S. Appl. No. 10/006,400, Mail Date May 24, 2006, Office Action.
U.S. Appl. No. 10/006,400, Mail Date Oct. 26, 2006, Office Action.
U.S. Appl. No. 10/006,400, Mail Date Apr. 19, 2007, Office Action.
U.S. Appl. No. 10/006,400, Mail Date Apr. 2, 2008, Office Action.
U.S. Appl. No. 10/006,400, Mail Date Jan. 2, 2009, Office Action.
U.S. Appl. No. 10/006,400, Mail Date Jul. 9, 2009, Notice of Allowance.
U.S. Appl. No. 10/006,400, Mail Date Jan. 13, 2010, Notice of Allowance.
U.S. Appl. No. 10/006,400, Mail Date Apr. 27, 2010, Notice of Allowance.
U.S. Appl. No. 10/006,400, Mail Date Aug. 2, 2010, Notice of Allowance.
U.S. Appl. No. 10/081,717, Mail Date Sep. 29, 2003, Notice of Allowance.
U.S. Appl. No. 10/081,723, Mail Date Sep. 29, 2004, Office Action.
U.S. Appl. No. 10/081,723, Mail Date May 13, 2005, Notice of Allowance.
U.S. Appl. No. 10/081,725, Mail Date Feb. 9, 2004, Notice of Allowance.
U.S. Appl. No. 10/081,725, Mail Date Apr. 13, 2004, Office Action.
U.S. Appl. No. 10/147,774, Mail Date Nov. 4, 2004, Office Action.
U.S. Appl. No. 10/147,774, Mail Date May 4, 2005, Office Action.
U.S. Appl. No. 10/147,774, Mail Date Oct. 18, 2005, Office Action.
U.S. Appl. No. 10/147,774, Mail Date Apr. 18, 2007, Notice of Allowance.
U.S. Appl. No. 10/147,774, Mail Date Sep. 27, 2007, Notice of Allowance.
U.S. Appl. No. 10/147,774, Mail Date Feb. 4, 2008, Notice of Allowance.
U.S. Appl. No. 10/147,774, Mail Date Jun. 30, 2008, Office Action.
U.S. Appl. No. 10/147,774, Mail Date Mar. 18, 2009, Office Action.
U.S. Appl. No. 10/147,774, Mail Date Oct. 26, 2009, Office Action.
U.S. Appl. No. 10/147,774, Mail Date Jun. 8, 2010, Office Action.
U.S. Appl. No. 10/147,774, Mail Date Dec. 2, 2010, Notice of Allowance.
U.S. Appl. No. 10/264,306, Mail Date Feb. 9, 2005, Office Action.
U.S. Appl. No. 10/264,306, Mail Date Oct. 4, 2005, Office Action.
U.S. Appl. No. 10/264,306, Mail Date May 10, 2006, Notice of Allowance.
U.S. Appl. No. 10/264,306, Mail Date Jul. 2, 2007, Notice of Allowance.
U.S. Appl. No. 10/264,306, Mail Date Feb. 4, 2008, Notice of Allowance.
U.S. Appl. No. 10/264,306, Mail Date Jun. 27, 2008, Office Action.
U.S. Appl. No. 10/264,306, Mail Date Feb. 26, 2009, Office Action.
U.S. Appl. No. 10/264,306, Mail Date Aug. 13, 2009, Office Action.
U.S. Appl. No. 10/264,306, Mail Date Jan. 27, 2010, Office Action.

(56) References Cited

OTHER PUBLICATIONS

U.S. Appl. No. 10/264,306, Mail Date Jun. 15, 2010, Office Action.
U.S. Appl. No. 10/264,306, Mail Date Oct. 29, 2010, Notice of Allowance.
U.S. Appl. No. 10/356,214, Mail Date Nov. 30, 2005, Office Action.
U.S. Appl. No. 10/356,214, Mail Date Aug. 23, 2006, Office Action.
U.S. Appl. No. 10/356,214, Mail Date Feb. 13, 2007, Office Action.
U.S. Appl. No. 10/356,214, Mail Date Sep. 12, 2007, Office Action.
U.S. Appl. No. 10/356,214, Mail Date Mar. 6, 2008, Office Action.
U.S. Appl. No. 10/356,214, Mail Date Nov. 4, 2008, Office Action.
U.S. Appl. No. 10/356,214, Mail Date Apr. 29, 2009, Office Action.
U.S. Appl. No. 10/356,214, Mail Date Jan. 13, 2010, Notice of Allowance.
U.S. Appl. No. 10/356,214, Mail Date May 13, 2010, Notice of Allowance.
U.S. Appl. No. 10/356,214, Mail Date Sep. 3, 2010, Notice of Allowance.
U.S. Appl. No. 10/638,115, Mail Date Sep. 22, 2006, Office Action.
U.S. Appl. No. 10/638,115, Mail Date Jan. 31, 2007, Office Action.
U.S. Appl. No. 10/638,115, Mail Date Sep. 18, 2007, Office Action.
U.S. Appl. No. 10/638,115, Mail Date Feb. 7, 2008, Office Action.
U.S. Appl. No. 10/638,115, Mail Date Oct. 29, 2008, Office Action.
U.S. Appl. No. 10/638,115, Mail Date May 7, 2009, Notice of Allowance.
U.S. Appl. No. 10/638,115, Mail Date Dec. 1, 2009, Notice of Allowance.
U.S. Appl. No. 10/638,115, Mail Date Apr. 2, 2010, Notice of Allowance.
U.S. Appl. No. 10/638,115, Mail Date Aug. 13, 2010, Notice of Allowance.
U.S. Appl. No. 10/638,115, Mail Date Dec. 22, 2010, Issue Notification.
U.S. Appl. No. 10/669,313, Mail Date Oct. 31, 2005, Office Action.
U.S. Appl. No. 10/669,313, Mail Date Jan. 11, 2006, Notice of Allowance.
U.S. Appl. No. 10/669,313, Mail Date Jun. 28, 2006, Notice of Allowance.
U.S. Appl. No. 10/682,459, Mail Date Sep. 15, 2006, Office Action.
U.S. Appl. No. 10/682,459, Mail Date Apr. 18, 2007, Office Action.
U.S. Appl. No. 10/682,459, Mail Date Apr. 2, 2008, Office Action.
U.S. Appl. No. 10/682,459, Mail Date Dec. 4, 2008, Office Action.
U.S. Appl. No. 10/682,459, Mail Date Jun. 10, 2009, Office Action.
U.S. Appl. No. 10/682,459, Mail Date Dec. 23, 2009, Office Action.
U.S. Appl. No. 10/682,459, Mail Date Apr. 28, 2010, Office Action.
U.S. Appl. No. 10/682,459, Mail Date Oct. 12, 2010, Office Action.
U.S. Appl. No. 10/682,459, Mail Date Apr. 1, 2011, Notice of Allowance.
U.S. Appl. No. 10/786,444, Mail Date Oct. 30, 2006, Office Action.
U.S. Appl. No. 10/786,444, Mail Date Apr. 17, 2007, Office Action.
U.S. Appl. No. 10/786,444, Mail Date Aug. 31, 2007, Office Action.
U.S. Appl. No. 10/786,444, Mail Date Apr. 24, 2008, Office Action.
U.S. Appl. No. 10/786,444, Mail Date Oct. 17, 2008, Office Action.
U.S. Appl. No. 10/786,444, Mail Date Jun. 18, 2009, Office Action.
U.S. Appl. No. 10/786,444, Mail Date Jan. 14, 2010, Office Action.
U.S. Appl. No. 11/048,503, Mail Date Mar. 13, 2009, Office Action.
U.S. Appl. No. 11/048,503, Mail Date Jun. 26, 2009, Office Action.
U.S. Appl. No. 11/048,503, Mail Date Jan. 11, 2010, Notice of Allowance.
U.S. Appl. No. 11/048,503, Mail Date Apr. 26, 2010, Notice of Allowance.
U.S. Appl. No. 11/048,503, Mail Date Jul. 30, 2010, Notice of Allowance.
U.S. Appl. No. 11/048,503, Mail Date Dec. 8, 2010, Issue Notification.
U.S. Appl. No. 11/198,811, Mail Date Aug. 26, 2008, Office Action.
U.S. Appl. No. 11/198,811, Mail Date Apr. 6, 2009, Office Action.
U.S. Appl. No. 11/198,811, Mail Date Sep. 22, 2009, Office Action.
U.S. Appl. No. 11/198,811, Mail Date Jun. 29, 2010, Notice of Allowance.
U.S. Appl. No. 11/198,811, Mail Date Oct. 20, 2010, Issue Notification.
U.S. Appl. No. 11/344,793, Mail Date Jan. 22, 2009, Office Action.
U.S. Appl. No. 11/344,868, Mail Date Mar. 25, 2009, Office Action.
U.S. Appl. No. 11/396,731, Mail Date Feb. 13, 2009, Office Action.
U.S. Appl. No. 11/396,731, Mail Date May 22, 2009, Office Action.
U.S. Appl. No. 11/396,731, Mail Date Jun. 29, 2010, Office Action.
U.S. Appl. No. 11/396,731, Mail Date Mar. 22, 2011, Office Action.
U.S. Appl. No. 11/406,203, Mail Date May 14, 2007, Office Action.
U.S. Appl. No. 11/406,203, Mail Date Jan. 29, 2008, Notice of Allowance.
U.S. Appl. No. 11/406,203, Mail Date May 23, 2008, Notice of Allowance.
U.S. Appl. No. 11/406,203, Mail Date Sep. 22, 2008, Notice of Allowance.
U.S. Appl. No. 11/406,203, Mail Date Mar. 3, 2009, Office Action.
U.S. Appl. No. 11/406,203, Mail Date Sep. 16, 2009, Office Action.
U.S. Appl. No. 11/406,203, Mail Date Jun. 18, 2010, Notice of Allowance.
U.S. Appl. No. 11/406,203, Mail Date Oct. 6, 2010, Issue Notification.
U.S. Appl. No. 11/411,925, Mail Date Jun. 6, 2007, Office Action.
U.S. Appl. No. 11/411,925, Mail Date Feb. 5, 2008, Office Action.
U.S. Appl. No. 11/411,925, Mail Date Jan. 12, 2009, Office Action.
U.S. Appl. No. 11/411,925, Mail Date Sep. 10, 2009, Office Action.
U.S. Appl. No. 11/427,297, Mail Date Jan. 30, 2009, Office Action.
U.S. Appl. No. 11/427,297, Mail Date Sep. 15, 2009, Office Action.
U.S. Appl. No. 11/427,297, Mail Date Sep. 15, 2010, Office Action.
U.S. Appl. No. 11/427,297, Mail Date Mar. 21, 2011, Office Action.
U.S. Appl. No. 11/532,325, Mail Date Feb. 23, 2009, Office Action.
U.S. Appl. No. 11/532,325, Mail Date Jun. 17, 2009, Office Action.
U.S. Appl. No. 11/532,325, Mail Date Jan. 5, 2010, Office Action.
U.S. Appl. No. 11/744,089, Mail Date Nov. 26, 2008, Office Action.
U.S. Appl. No. 11/744,089, Mail Date Aug. 14, 2009, Office Action.
U.S. Appl. No. 11/852,190, Mail Date Jun. 24, 2010, Office Action.
U.S. Appl. No. 11/852,190, Mail Date Nov. 1, 2010, Office Action.
U.S. Appl. No. 11/852,190, Mail Date Mar. 2, 2011, Office Action.
U.S. Appl. No. 12/106,928, Mail Date Jan. 23, 2009, Office Action.
U.S. Appl. No. 12/106,928, Mail Date Oct. 5, 2009, Office Action.
U.S. Appl. No. 12/106,928, Mail Date May 10, 2010, Office Action.
U.S. Appl. No. 12/106,928, Mail Date Oct. 25, 2010, Office Action.
U.S. Appl. No. 12/106,937, Mail Date Mar. 30, 2009, Office Action.
U.S. Appl. No. 12/106,937, Mail Date Nov. 18, 2009, Office Action.
U.S. Appl. No. 12/143,020, Mail Date May 11, 2011, Office Action.
U.S. Appl. No. 13/525,718, filed Jun. 18, 2012, Carley et al.
U.S. Appl. No. 12/941,809, Mail Date Jun. 1, 2012, Office Action.
U.S. Appl. No. 12/955,859, Mail Date May 26, 2011, Office Action.
U.S. Appl. No. 11/427,297, Mail Date Jun. 26, 2012, Notice of Allowance.
U.S. Appl. No. 13/039,087, Mail Date Jul. 17, 2012, Office Action.
U.S. Appl. No. 12/135,858, Mail Date Jul. 13, 2011, Office Action.
U.S. Appl. No. 12/955,859, Mail Date Jul. 21, 2011, Office Action.
U.S. Appl. No. 10/682,459, Mail Date Aug. 10, 2011, Office Action.
U.S. Appl. No. 11/675,462, Mail Date Aug. 15, 2012, Issue Notification.
U.S. Appl. No. 11/744,089, Mail Date Aug. 8, 2012, Office Action.
U.S. Appl. No. 12/481,377, Mail Date Aug. 10, 2012, Notice of Allowance.
U.S. Appl. No. 12/955,859, Mail Date Aug. 6, 2012, Office Action.
U.S. Appl. No. 12/143,020, Mail Date Aug. 31, 2011, Office Action.
U.S. Appl. No. 11/396,731, Mail Date Sep. 1, 2011, Office Action.
U.S. Appl. No. 12/393,877, Mail Date Sep. 29, 2011, Office Action.
U.S. Appl. No. 11/427,297, Mail Date Oct. 31, 2012, Issue Notification.
U.S. Appl. No. 13/039,087, Mail Date Nov. 6, 2012, Notice of Allowance.
U.S. Appl. No. 12/961,331, Mail Date Dec. 4, 2012, Office Action.
U.S. Appl. No. 13/488,233, Mail Date Jun. 5, 2013, Issue Notification.
U.S. Appl. No. 11/744,089, Mail Date Aug. 8, 2013, Notice of Allowance.
U.S. Appl. No. 12/955,859, Mail Date Aug. 1, 2013, Notice of Allowance.

(56) References Cited

OTHER PUBLICATIONS

U.S. Appl. No. 13/615,547, Mail Date Aug. 7, 2013, Issue Notification.
U.S. Appl. No. 13/791,829, filed Mar. 8, 2013, Roorda et al.
U.S. Appl. No. 13/791,846, filed Mar. 8, 2013, Palermo.
U.S. Appl. No. 13/898,202, filed May 20, 2013, Walberg et al.
U.S. Appl. No. 11/744,089, Mail Date Apr. 15, 2013, Office Action.
U.S. Appl. No. 11/852,190, Mail Date Apr. 24, 2013, Office Action.
U.S. Appl. No. 12/955,859, May 16, 2013, Office Action.
U.S. Appl. No. 13/052,634, Mail Date Feb. 8, 2013, Restriction Requirement.
U.S. Appl. No. 13/052,634, Mail Date Apr. 22, 2013, Office Action.
U.S. Appl. No. 13/308,227, Mail Date Apr. 10, 2013, Office Action.
U.S. Appl. No. 13/490,143, Mail Date Apr. 29, 2013, Notice of Allowance.
U.S. Appl. No. 13/615,547, Mail Date Apr. 12, 2013, Notice of Allowance.
U.S. Appl. No. 12/106,928, Mail Date Jun. 28, 2013, Office Action.
U.S. Appl. No. 12/941,809, Mail Date Jul. 3, 2013, Office Action.
U.S. Appl. No. 12/961,331, Mail Date Jul. 3, 2013, Office Action.
U.S. Appl. No. 10/786,444, Mail Date Jul. 11, 2013, Notice of Allowance.
U.S. Appl. No. 11/532,325, Mail Date Jul. 17, 2013, Office Action.
U.S. Appl. No. 13/615,547, Mail Date Jul. 10, 2013, Issue Notification.

\* cited by examiner

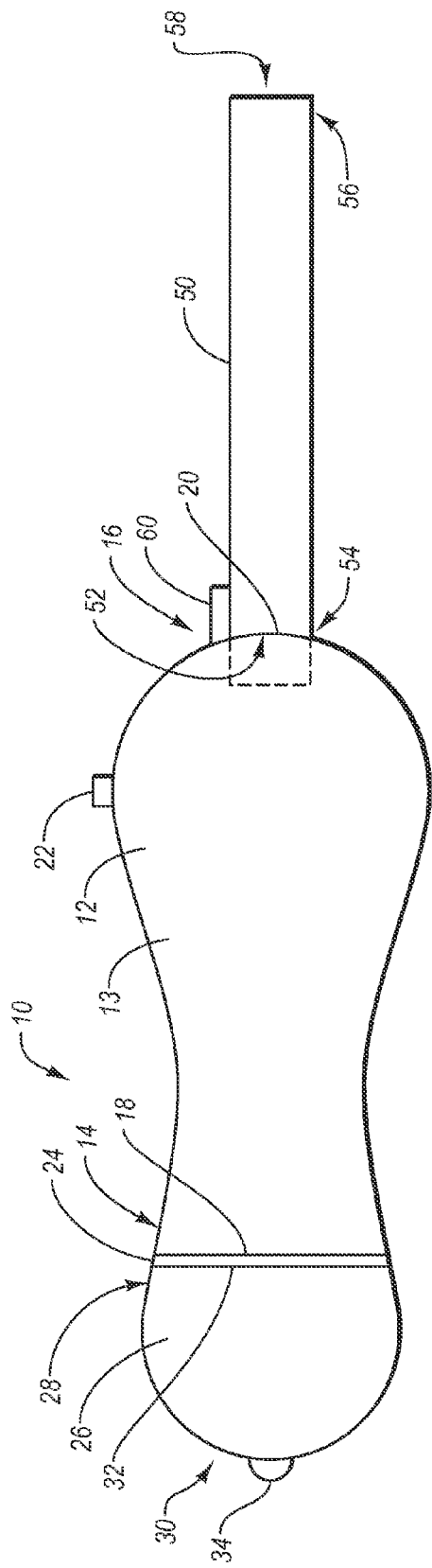

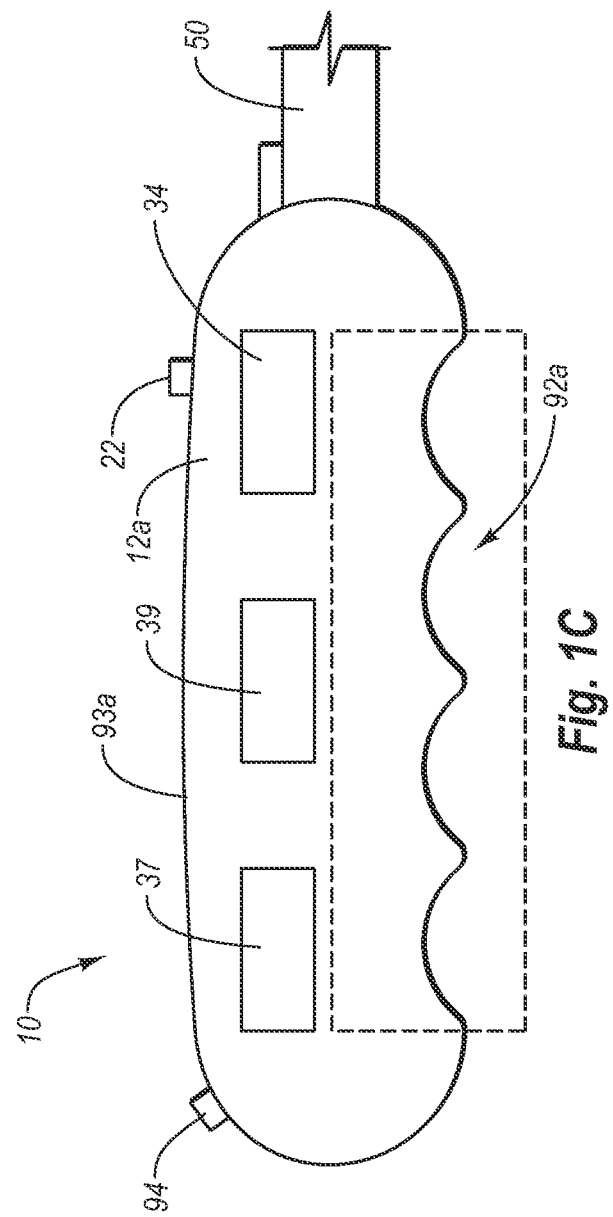

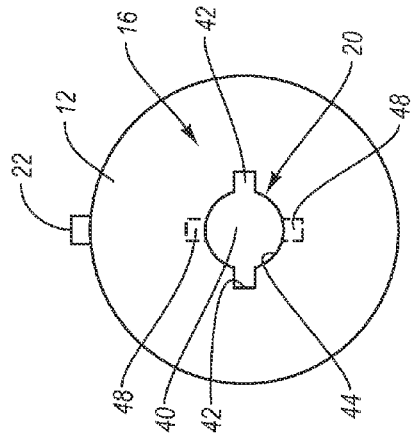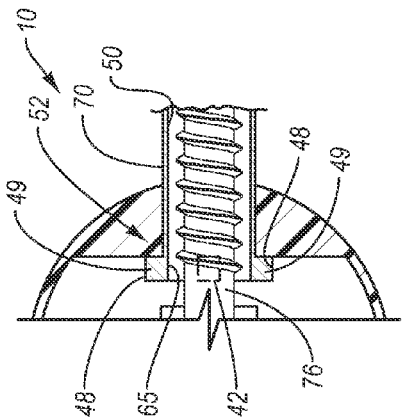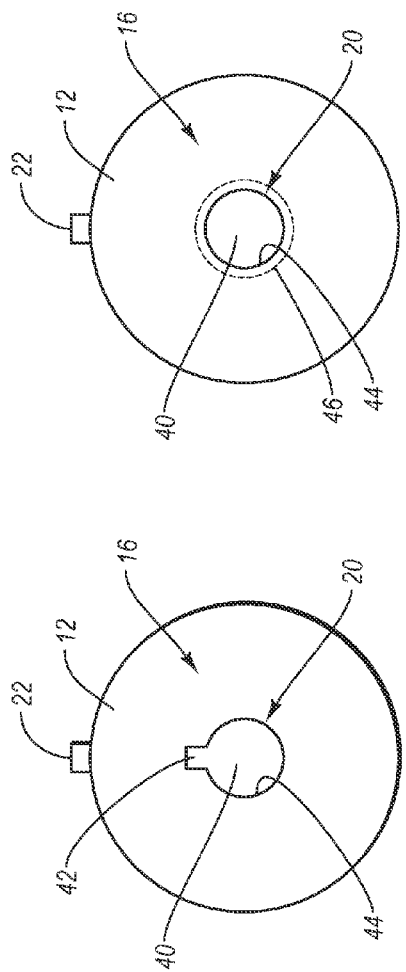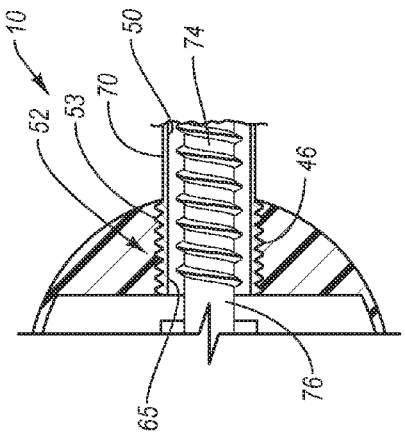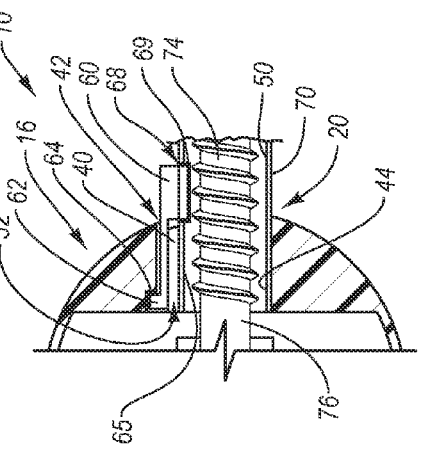

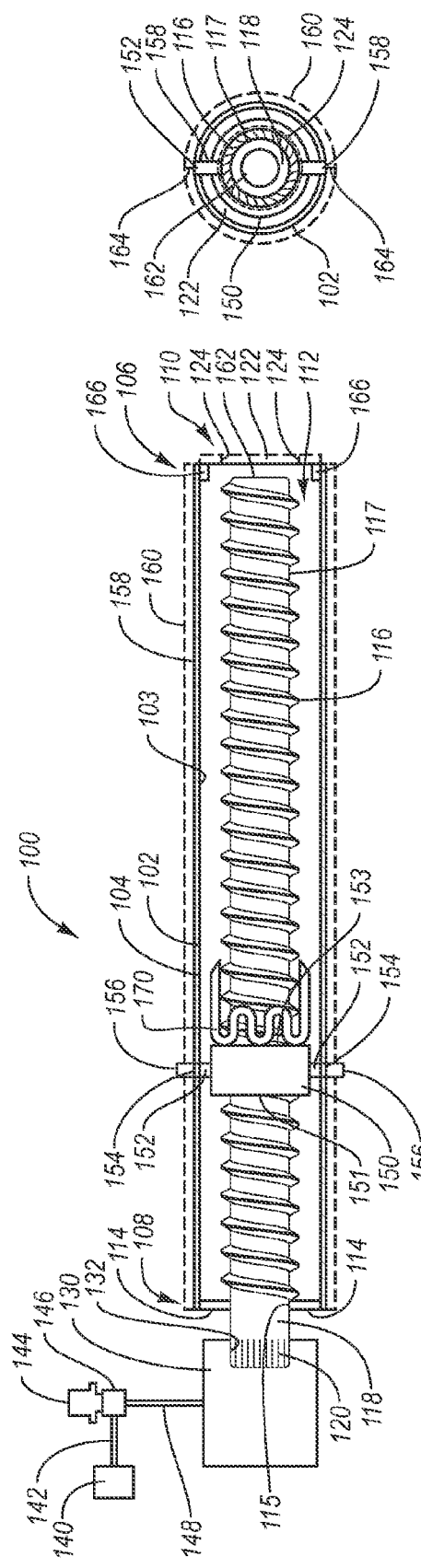
Fig. 5A
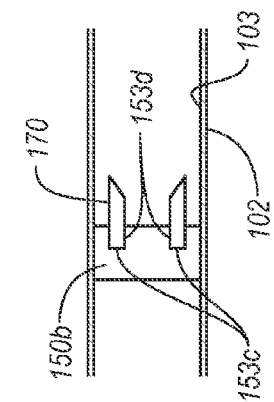
Fig. 5B
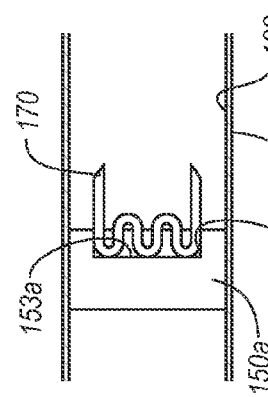
Fig. 5C
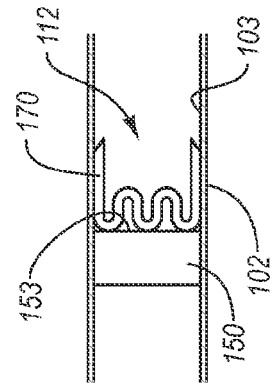
Fig. 5D
Fig. 5E

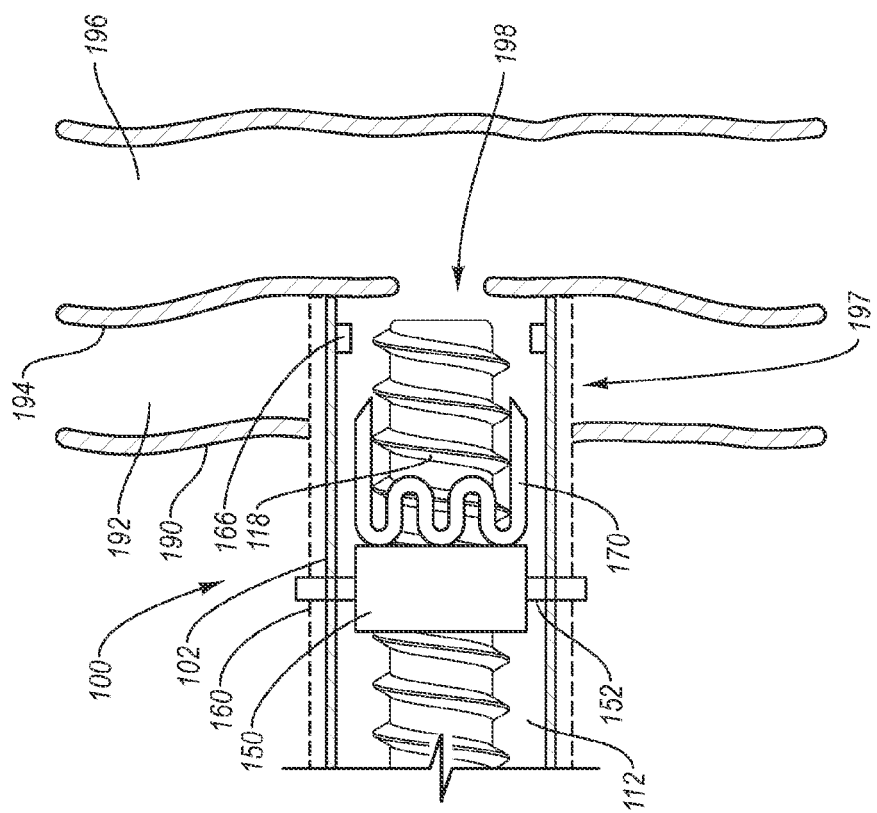
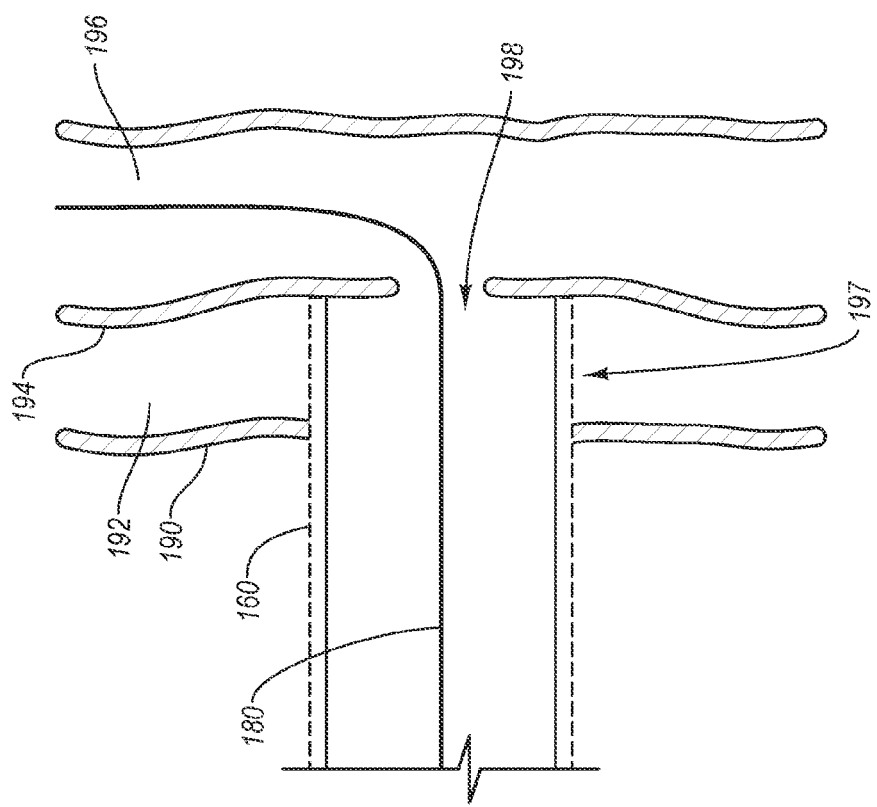

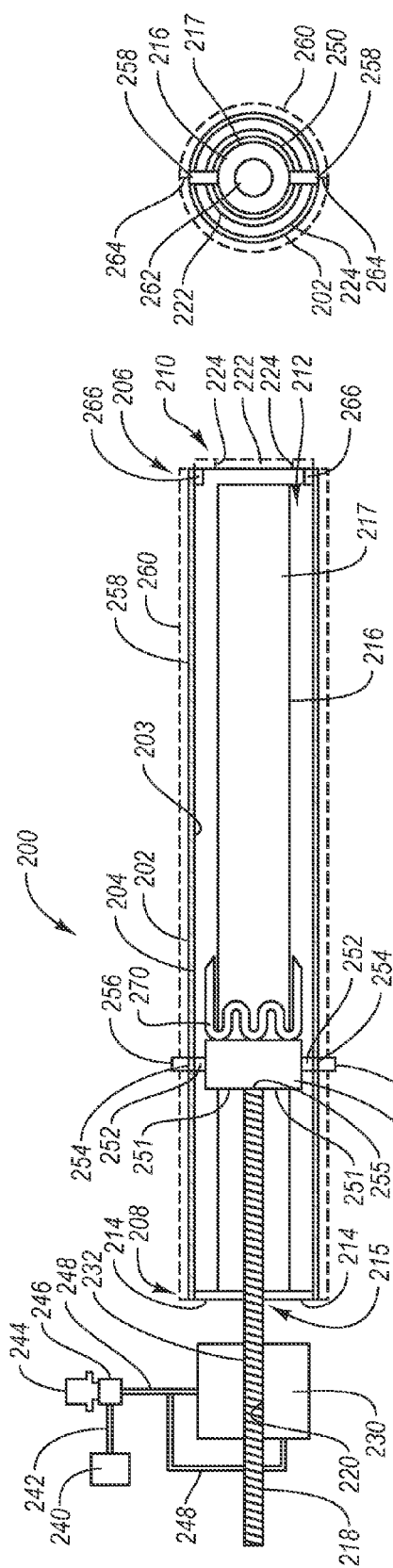
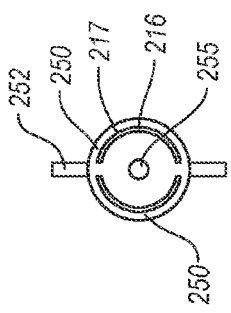
Fig. 7A
Fig. 7B
Fig. 7C

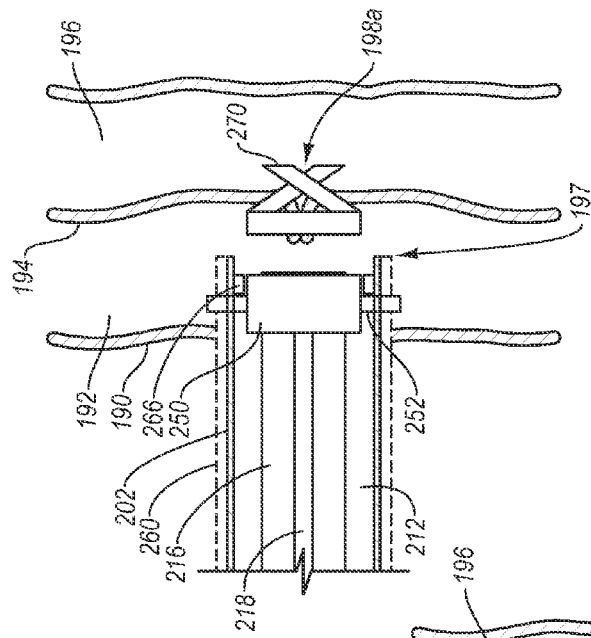
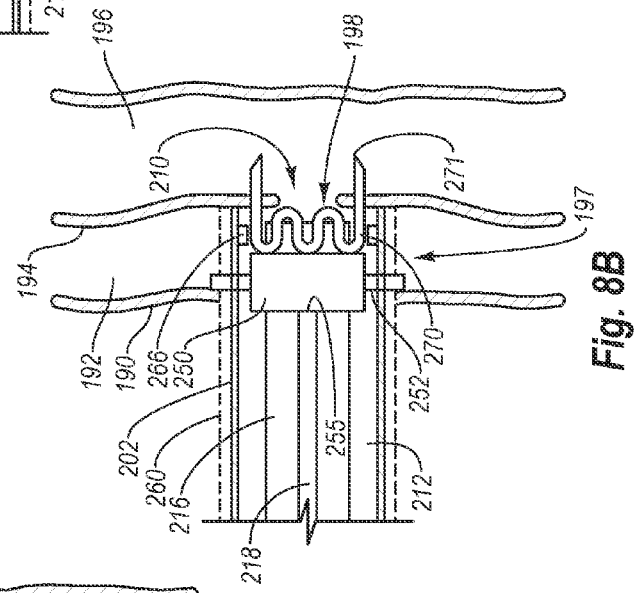
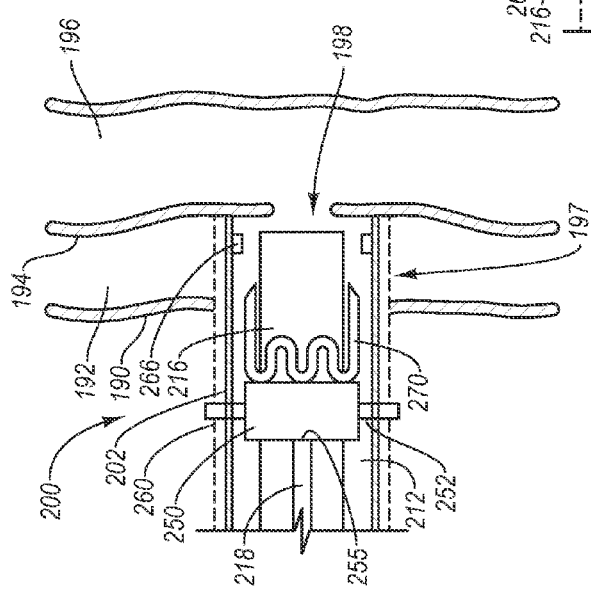
Fig. 8A
Fig. 8B
Fig. 8C

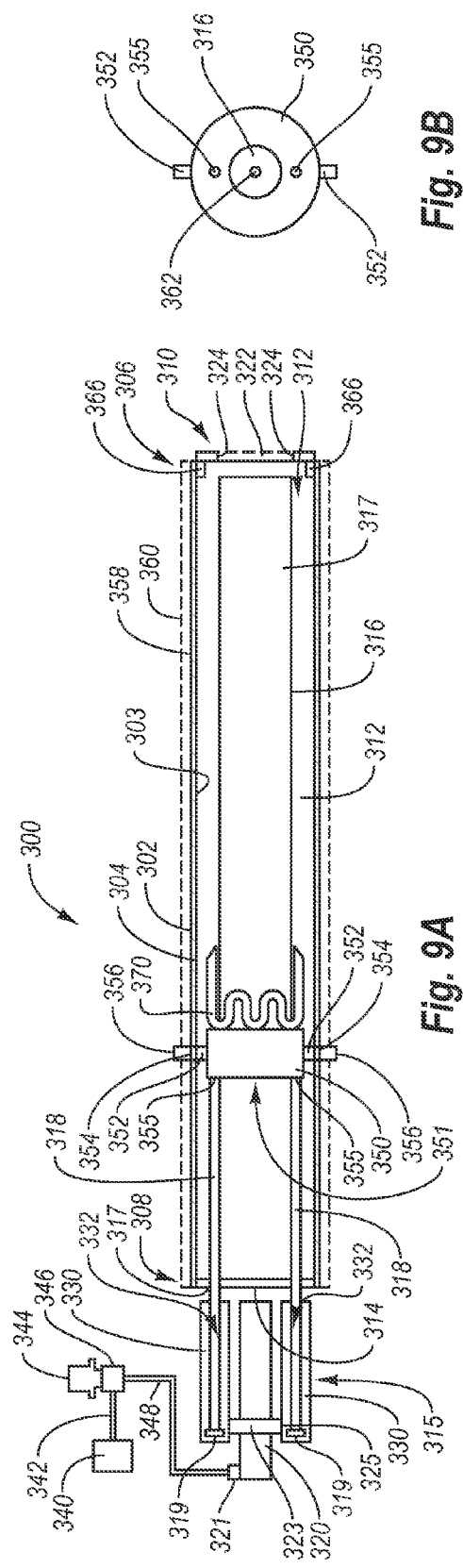

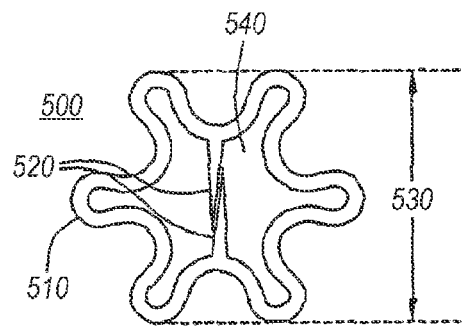
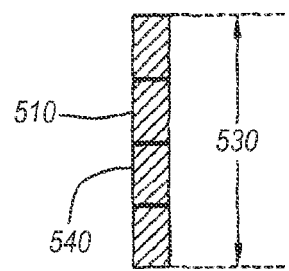
Fig. 11A    Fig. 11B
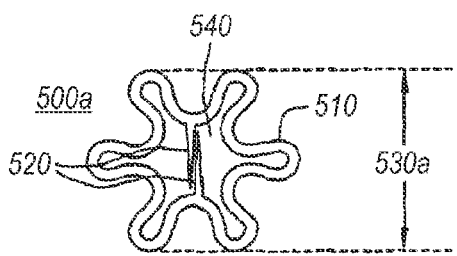
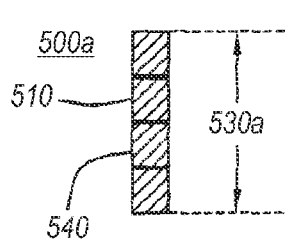
Fig. 11C    Fig. 11D
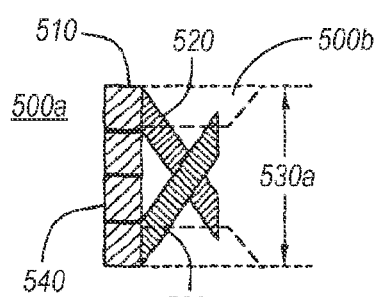
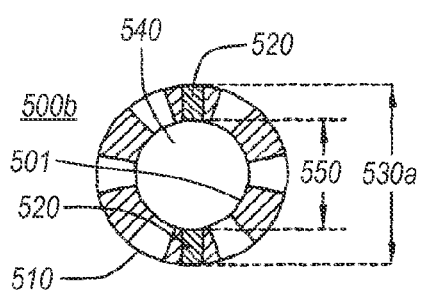
Fig. 11E    Fig. 11F
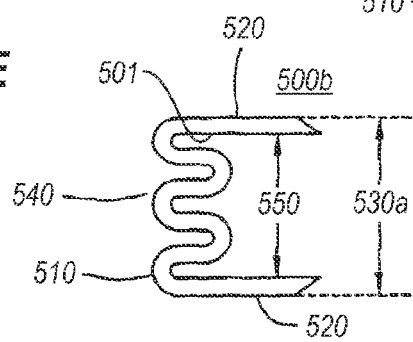
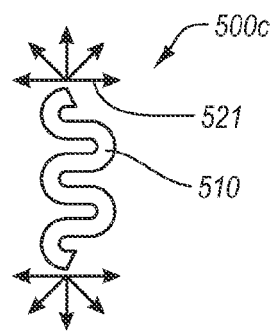
Fig. 11G    Fig. 11H

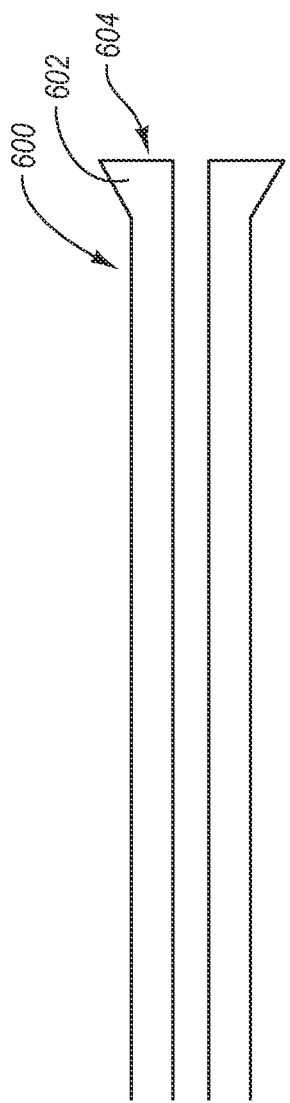
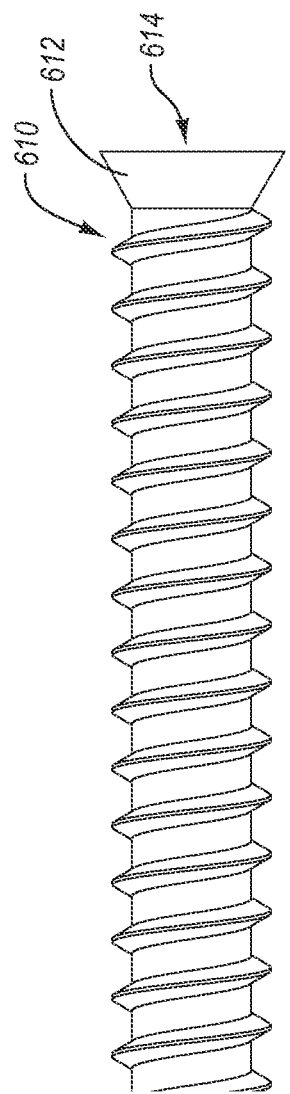
Fig. 12A
Fig. 12B

VESSEL CLOSURE SYSTEM

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle is then removed, enabling an introducer sheath to be advanced over the guide wire into the vessel, e.g., in conjunction with or subsequent to a dilator. A catheter or other device may then be advanced through a lumen of the introducer sheath and over the guide wire into a position for performing a medical procedure. The introducer sheath may facilitate introducing various devices into the vessel, while minimizing trauma to the vessel wall and/or minimizing blood loss during a procedure. Upon completing the procedure, the devices and introducer sheath are usually removed, leaving a puncture site in the vessel wall.

Traditionally, external pressure was applied to the puncture site until clotting and wound sealing occurred. In addition, the patient typically remained bedridden for a substantial period of time after clotting to ensure closure of the wound. This procedure was typically time consuming and expensive, and often required as much as an hour of a physician's or nurse's time. It was also uncomfortable for the patient, and required that the patient remain substantially immobilized in the operating room, catheter lab, or holding area. In addition, a risk of hematoma existed from bleeding before hemostasis occurs.

Various medical devices have been utilized in order to close and seal the puncture site in the vessel wall. These medical devices have varied in configuration as well as in the closure device that actually closes the puncture site. The closure devices have ranged from clips that function similar to staples, to patches, and to plugs that occlude the puncture site. While the medical devices and corresponding closure devices have been successful to a certain degree, the functionality and operability of these medical devices has remained tedious and difficult. The various actuating members and modes of actuation that must be operated or controlled are difficult for a single person to perform. For example, a clip applier may be configured to successfully close a puncture site in a vessel wall; however, the operability of the clip applier may be difficult to control and require an enormous amount of manual dexterity.

BRIEF SUMMARY OF THE INVENTION

In one embodiment, a power driven vessel closure system can include a handle and one or more sheaths. The handle can include a power operated drive system. Each sheath can have a proximal end being removably couplable with the handle. Also, each sheath can include: an elongate drive member having a proximal end that is removably and operably couplable with the power operated drive system; and a closure element removably and operably coupled with the elongate drive member, said closure element being retained in the sheath in a storage orientation, and when said elongate drive member is operably coupled to the power operated drive system said elongate drive member is capable of distally moving the closure element within the sheath to the distal end of the elongate drive member and releasing the closure element from the elongate drive member and sheath into the wall of the body lumen so as to convert the closure element to a closed orientation and close the hole.

In one embodiment the vessel closure system can include at least one of the following: one or more buttons disposed on the handle configured for manual actuation, wherein manual actuation of the button is capable of causing the power operated drive system to deliver the closure element into the wall of the body lumen so that the closure element converts to the closed orientation and closes the hole in the wall of the body lumen; one or more power sources, each including at least one of a power converter electronically couplable to an external power supply, a battery, a rechargeable battery, a pressurized fluid chamber, multiples thereof, and combinations thereof; one or more mechanical drive systems associated with or part of the power operated drive system, each including at least one of a motor, a transmission, gearing, a worm gear, a servomotor, a biased member having potential energy, a pump, a pressurized fluid chamber, a pressurized hydraulic chamber, multiples thereof, or combinations thereof; one or more of a worm drive system, plunger, shaft, hollow tube, threaded shaft, telescoping shaft, multiples thereof, or combinations thereof associated with or part of the one or more mechanical drive systems; one or more drive collars operably coupled with the elongate drive member and the closure element, said drive collar being configured to distally move the closure element within the sheath; or one or more protective devices, each having an internal chamber configured to receive the handle such that the elongate drive member extends out from the internal chamber. Also, the sheath can include a lumen having at least a portion of an elongate drive member, a drive collar, and the closure element, said elongate drive member being operably coupled with the drive collar which is associated with the closure element, said sheath having a distal end that is configured to release the closure element from the drive collar and into the wall of the body lumen. Optionally, the sheath is disposable.

In one embodiment, a power driven vessel closure system can include: a power source; a driver system operably couplable with the power source; an elongate drive member removably and operably couplable to the driver system; a drive collar operably coupled to the elongate drive member; and a closure element associated with a surface of the drive collar, said closure element being retained in the vessel closure system in a deployment orientation and being capable of converting to a closed orientation when released from the vessel closure system into a wall of a body lumen so as to close the hole.

In one embodiment, a protective device is included. The protective device can include an internal chamber that is configured to receive the handle and the proximal end of the elongate drive member such that a distal end of the elongate drive member extends out from the internal chamber. The protective device can also include an openable sealing mechanism that is configured to open to receive the handle and to close and provide a fluid-tight seal. The protective device can include an aperture opposite of the openable sealing mechanism, where the aperture can configured to receive the proximal end of a sheath therethrough so as to provide a fluid-tight seal with the sheath with a distal end of the sheath extending from the protective device.

In one embodiment, the present invention can include a kit that has a handle as described herein and a plurality of sheaths (e.g., optionally disposable). Also, a plurality of protective devices can be included in the kit.

In one embodiment, the present invention can include a method for performing a medical procedure, such as closing a hole in a blood vessel with a vessel closure device. The method can include actuating a control member so as to cause electric power to operate a mechanical driver system to move a closure element in a distal direction until tines of the closure element penetrates the blood vessel proximal to the hole, and the closure element reverts in shape from a storage orientation to a closed orientation which closes the hole by pulling portions of the blood vessel surrounding the hole together.

In one embodiment, the method can include inserting a distal end of a sheath that contains the closure element through the skin, and positioning a distal end of the sheath at the hole. Also, the actuated control member can be a button that is actuated by: pressing the button to move the closure element in the distal direction so as to close the hole in the blood vessel, and releasing the button after the closure element has closed the hole. Additionally, the method can include performing a diagnostic protocol with the vessel closure device to determine whether an electrical power source has sufficient power to move the closure element in the distal direction and close the hole in the blood vessel. For example, the diagnostic protocol can cause an indicator to provide a first indication when the power source has sufficient power and to provide a second indication when the power source does not have sufficient power.

In one embodiment, actuating the control member can cause a power source to provide power to a driver system that operates an elongate drive member that drives the closure element in a distal direction.

In one embodiment, the handle can be disposed within a protective device such that a distal end of a sheath of the vessel closure device extends through an aperture of the protective device. Optionally, the protective device can be sealed with the handle disposed therein so as to provide a fluid-tight seal with the sheath extending from the protective device.

In one embodiment, the method can include at least one of the following: coupling the sheath and the handle; removing the sheath from the handle after the hole has been closed with the closure element; removing the handle from a protective device; disposing of the sheath as waste; sanitizing the handle for reuse; or the like.

In one embodiment, the method can include removing a first sheath from the handle after a first medical procedure, and coupling a second sheath to the handle and performing a second medical procedure.

These and other embodiments and features of the present invention will become more fully apparent from the following description and appended claims, or may be learned by the practice of the invention as set forth hereinafter.

BRIEF DESCRIPTION OF THE DRAWINGS

To further clarify some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1A is a side view illustrating an embodiment of a vessel closure device.

FIG. 1B is a cutaway side view illustrating internal components of the vessel closure device of FIG. 1A.

FIG. 1C is a side view illustrating an embodiment of an ergonomic handle for a vessel closure device.

FIG. 2A is a frontal view illustrating an embodiment of a coupling recess for receiving a closure element housing.

FIG. 2B is a cutaway side view illustrating an embodiment of a closure element housing in accordance with FIG. 2A.

FIG. 3A is a frontal view illustrating an embodiment of a coupling recess for receiving a closure element housing.

FIG. 3B is a cutaway side view illustrating an embodiment of a closure element housing in accordance with FIG. 3A.

FIG. 4A is a frontal view illustrating an embodiment of a coupling recess for receiving a closure element housing.

FIG. 4B is a cutaway side view illustrating an embodiment of a closure element housing in accordance with FIG. 4A.

FIG. 5A is a cutaway side view illustrating internal components of an embodiment of a vessel closure device.

FIG. 5B is a cutaway cross-sectional frontal view illustrating the closure element housing of the vessel closure device of FIG. 5A.

FIGS. 5C-5E are cutaway side views that illustrate different embodiments of drive collars in regard to the sheath/garage and the closure element.

FIGS. 6A-6D are schematic representations illustrating a method for closing an opening in a body vessel with the vessel closure device of FIGS. 5A-5B.

FIG. 7A is a cutaway side view illustrating internal components of an embodiment of a vessel closure device.

FIG. 7B is a cutaway cross-sectional frontal view illustrating the closure element housing of the vessel closure device of FIG. 7A.

FIG. 7C is a cutaway cross-sectional frontal view illustrating another embodiment of a closure element housing of the vessel closure device of FIG. 7A.

FIGS. 8A-8C are schematic representations illustrating a method for closing an opening in a body vessel with the vessel closure device of FIGS. 5A-5B.

FIG. 9A is a cutaway side view illustrating internal components of an embodiment of a vessel closure device.

FIG. 9B is a cutaway cross-sectional frontal view illustrating the closure element housing of the vessel closure device of FIG. 9A.

FIGS. 11A-11H are various views that illustrate an embodiment of a closure element.

FIG. 12A illustrates an embodiment of a carrier tube having a distal outward taper for expanding a closure element.

FIG. 12B illustrates an embodiment of a drive shaft having a distal outward tapered member for expanding the closure element.

DETAILED DESCRIPTION OF THE PREFERRED EMBODIMENTS

Figure 6D:
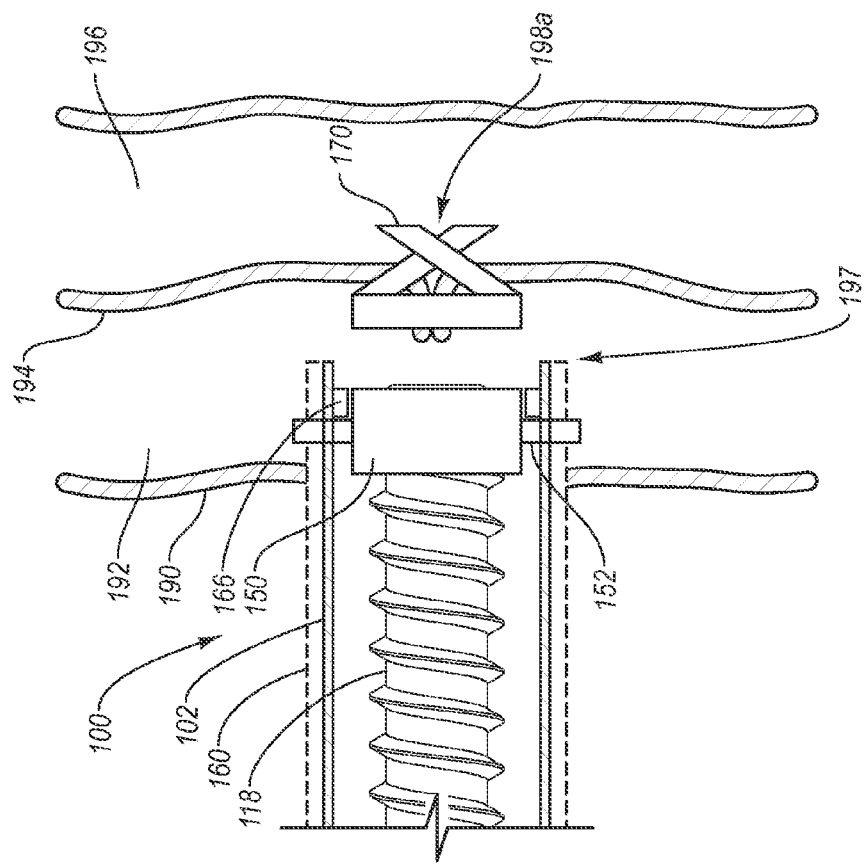

Generally, embodiments of the present invention relate to a medical device for repairing an opening in a body lumen, such as a blood vessel, urethra, or the like and to methods for repairing an opening in a body lumen. The opening can be any type of opening that provides an abnormal or non-natural channel into a body lumen. The medical device can be configured to repair any type of opening in a body lumen at any location within the body of a subject. Embodiments of the invention can be further adapted to performing medical procedures that may include repairing an opening in a body lumen, for example, to repair an arteriotomy.

A medical device for repairing an opening in a body lumen may have an elongate member with an internal lumen housing a closure element. The closure element may be configured for delivery into tissue surrounding an opening in a body lumen. When deployed, the closure element repairs or closes or substantially closes the opening. The closure element can be applied to the tissue on the outer edge or internal surface or any other location related to the opening in order to repair the body lumen to prevent fluid leakage or for other reasons.

The vessel closure device can be configured to receive and retain the closure element such that the closure element is disposed substantially within a "garage" that is configured to hold and/or configure the closure element for deployment. When the vessel closure device is introduced into the body of a subject, such as via an introducer sheath, for example, the closure element can be disposed within, and delivered by way of, a lumen of the introducer sheath. The vessel closure device also can be configured to engage the blood vessel wall (or other body lumen wall) adjacent to the opening and to position the closure element substantially adjacent to an outer surface of the blood vessel wall adjacent to the opening.

When properly positioned, the vessel closure device can be activated to distally deploy the closure element. During deployment, the vessel closure device can be configured to expand the closure element beyond a natural cross-section of the closure element (e.g., in a storage orientation) such that the closure element engages a significant or sufficient amount of the blood vessel wall and/or tissue surrounding and/or adjacent to the hole. After engaging the blood vessel wall and/or other tissue, the closure element can be further configured to return to the natural orientation, such as the substantially closed orientation. As the closure element returns to a closed orientation, the engaged blood vessel wall and/or tissue is drawn substantially closed and/or sealed, such that, for example, hemostasis within the opening is enhanced.

Embodiments of the invention include medical devices that are configured to prevent inadvertent tissue contact during positioning and to engage a substantial or sufficient amount of tissue adjacent to the opening. This can prove much more desirable and provide a basis for a wide range of medical applications, such as diagnostic and/or therapeutic procedures involving blood vessels or other body lumens of any size. Embodiments of the invention further include medical devices, such as vessel closure devices that are power operated and that allow a medical practitioner to operate the device with one hand, such as by the push of a button. Embodiments of the invention thus provide an ergonomic, including ease of use, medical device. In addition, embodiments of the invention further include medical devices that are reusable, disposable, partially disposable, and the like.

In one embodiment, the present invention can include a power driven vessel closure device that is configured for closing a hole in a wall of a body lumen, such as a blood vessel. While the device can be used to close a hole in any body lumen, an advantageous use of the device is to close an arteriotomy in a blood vessel. As such, the device can generally be referred to as a vessel closure device. The vessel closure device can include a power operated drive system and a closure element delivery system. The closure element delivery system can be removably, operably, couplable with the power operated drive system. That is, the closure element system can be attached to and removed from the power operated drive system, or components thereof. The operation of the power operated drive system can operate the closure element delivery system so as to move the closure element within the vessel closure device to deliver or deploy the closure element to close or substantially close the hole or other opening in a lumen. The closure element (or closure element delivery system) can be directly or indirectly coupled with the drive system.

The closure element can be retained in a garage (e.g., within the lumen of a tubular sheath) of the vessel closure device in a storage orientation and when moved by the power operated drive system to a terminal position in the garage, the closure element can convert from the storage orientation to a closed orientation as the closure element is released from the garage or when the closure element is expelled from the sheath. The power operated drive system thereby can cause the closure element to be delivered into a wall of the body lumen (e.g., blood vessel) so as to close the hole (e.g., arteriotomy).

In one embodiment, the vessel closure device can include a power driven vessel closure system that is configured for closing a hole in a wall of a body lumen, such as a blood vessel. The vessel closure system includes a handle that may be separate and removably couplable with a sheath that houses a closure element. The handle can be configured to contain the components that operate the device and/or provide power to the device, while the sheath can be configured to contain disposable components that retain and/or deploy the closure element. The vessel closure system can include a power source, a drive system, an elongate drive member (e.g., drive shaft), a drive collar, and a closure element. The handle can contain the power source and the driver system which can be operably coupled with the power source, and optionally decouplable therefrom. The elongate drive member can be removably, operably, couplable to the driver system, and thereby can be coupled to the driver system and be removable therefrom. The elongate drive member can be at least partially disposed in the sheath and/or at least partially disposed in the handle.

For example, the portions of the elongate drive member that couple with the drive system can be coupled with the drive system such that a portion is disposed within the handle, and the portions of the elongate drive member that couple with the drive collar and/or closure element can be disposed within the sheath. The drive collar can be disposed in the sheath and be operably coupled to the elongate drive member such that operation of the elongate drive member by the driver system can move the drive collar in a distal and/or proximal direction depending on the mode of operation. The closure element can be disposed in the sheath and associated with a surface of the drive collar and/or elongate drive member. The closure element can be retained in the sheath in a storage orientation, and can be capable of converting to a closed orientation when released from the vessel closure system into a wall of a body lumen so as to close the hole.

In one embodiment, the vessel closure system can be used in a method for closing a hole in a blood vessel with a vessel closure device as described herein. Accordingly, the method can include actuating a control member (e.g., button) so as to cause electric power (e.g., from a power source) to operate a mechanical driver system (e.g., motors, pumps, compressors, etc.) to move a closure element in a distal direction until tines (e.g., sharp points) of the closure element penetrates the blood vessel proximal to the hole. After the closure element penetrates the blood vessel it can be released from the garage/sheath so that the closure element can convert in shape from a storage orientation (e.g., substantially tubular) to a closed orientation (e.g., substantially planar) which closes the hole by pulling portions of the blood vessel surrounding the hole together. The tines engage the blood vessel around or proximal to the hole. When the closure element converts in shape, the blood vessel is pulled inwardly to close the hole.

I. Vessel Closure

In one embodiment, the present invention can include a power driven vessel closure device for closing a hole or opening in a wall of a body lumen, such as a blood vessel. While the device can be used to close any hole in any body lumen, an advantageous use of the device can be to close an arteriotomy in a blood vessel. As such, the device can generally be referred to as a vessel closure device. The vessel closure device can include a power operated drive system and a closure element. The closure element can be directly or indirectly removably, operably, couplable with the power operated drive system. The closure element can be disposed on a drive shaft, which may be considered part of the power operated drive system, or the closure element can be associated with a drive collar that is operably coupled with the drive shaft. In any event, the operation of the power operated drive system can move the closure element within or relative to the vessel closure device.

For example, one or more components can be disposed between a mechanical device and the closure element in a manner that operation of the mechanical device can move the closure element. The closure element can be retained in a garage (e.g., lumen or sheath) of the vessel closure device in a storage orientation and when moved by the power operated drive system to a terminal position in the garage, the closure element can convert from the storage orientation to a closed orientation as the closure element is released from the garage. The power operated drive system thereby can cause the closure element to be delivered into a wall of the body lumen (e.g., blood vessel) or deployed so as to close the hole or opening.

The vessel closure device can be prepared by or include materials that are commonly used in medical devices and can include internal components of common battery operated mechanical devices that have electronics. The external materials can be biocompatible such as biocompatible polymers, metals, ceramics, and the like. The mechanical components that are disposed within the device can have various materials, which may not need to be biocompatible because they do not contact the body. Embodiments of the vessel closure device can include both biocompatible materials and non-biocompatible materials. For example, the vessel closure device can include a handle that is formed from stainless steel and the sheath can be a biocompatible polymer. Other materials may be suitable for constructing the vessel closure device. Metals such as anodized aluminum or cobalt-chromium allows, or polymers such as ABS or fluoroplastics may be suitable for the handle. The sheath can be made from a variety of polymers, such as polyamides, polyurethanes, silicone modified polyurethanes, fluoropolymers, polyolefins, or polyimides.

In one embodiment, a vessel closure device can include at least one control member, such as a button, configured for manual actuation. Manual actuation of the control member is capable of causing the power operated drive system to deliver the closure element into the wall of the body lumen so that the closure element converts to the closed orientation and closes the hole in the wall of the body lumen. Other examples of a control member can include dials, switches, knobs, levers, touch screens, voice-operated components, or the like. Any device that can be manually or otherwise actuated can be used for a control member so as to be capable of controlling the function of the vessel closure device.

A vessel closure device may include a power operated drive system that has a power source with at least one of a power converter electronically couplable to an external power supply, a battery, a rechargeable battery, a pressurized fluid chamber, and/or combinations thereof. Any component or device that can store and provide power can be used. As such, any device, battery, plug, power supplier, or the like that can provide power, such as electrical power, can be used to power the vessel closure device. Other power devices, such as those with potential energy that can be converted to kinetic energy to move the closure element can be included. The power source can provide power to the device when the control member is actuated by an operator.

In one embodiment, a vessel closure device can include a power operated drive system that operates mechanical components to deliver the closure element and close, seal, or substantially seal the hole in the blood vessel or other lumen. The power source can provide power to the drive system when the control member is actuated by an operator.

The power operated drive system can include one or more components that are power operated. This can include a mechanical system that receives power from the power source. The mechanical components can be part of a mechanical drive system that includes at least one of a motor, a transmission, gearing, a worm gear, a servomotor, a biased member having potential energy, a pump, a compressor, a pressurized fluid chamber, a pressurized hydraulic chamber, or combinations thereof. Any device or mechanical system that can provide energy or power to deliver, position, and/or deploy the closure element can be included. The drive system can be configured similarly to any other mechanical drive system or type of system that can move an object. Also, the drive system can include electric motors. Additionally, the drive system can use piezo linear motors.

The drive system can include a preloaded mechanical spring in place of a traditional electronic motor. The preloaded spring can be configured to release energy on command from the user so as to function similarly to a motor. Also, the drive system can be pressure based and can use a gas (e.g., air, oxygen, nitrogen, carbon dioxide, etc.) at an elevated pressure to provide a force to push the closure element or provide power for other aspects of the medical device. The pressure based drive system can use a pressure cartridge and plunger mechanism, for example.

In one embodiment, a vessel closure device can include a mechanical drive system that operates an elongate drive member (e.g., drive shaft) that delivers the closure element to the appropriate location or position. The elongate drive member can be configured to be include at least one of a worm drive system, plunger, shaft, hollow tube, threaded shaft, telescoping shaft, or combinations thereof. The elongate drive member can be any member that is elongate, hollow or solid, that can be configured with a drive system to cause a closure element to be deployed into a vessel wall. Any mechanical drive system that utilizes an elongate member to distally drive a closure element can be used in the vessel closure device.

In one embodiment, a vessel closure device can include an elongate sheath for the closure element. Also, "garage" can be a general term for the portion of the elongate sheath that is configured to retain the closure element and release the closure element therefrom so as to function as a garage. For example, the lumen of the elongate sheath can be referred to as a garage for the closure element, and the elongate sheath can include a distal end configured as a "garage door" that can be closed while retaining the closure element and then open to release and deploy the closure element.

The sheath can be removably couplable to a handle through various fastener, coupling, or connecting mechanisms. That is, the sheath can be coupled to the handle for use in closing a hole in a blood vessel, and then detached therefrom so that the handle can be sanitized and reused. The sheath can be reconditioned with a new closure element for reuse, or can be disposable as waste. Inexpensive polymer components can allow the garage to be disposable. Thus, embodiments of the medical device can be reusable, partially reusable, disposable, and/or partially disposable.

In one embodiment, a sheath can be configured to contain at least a portion of the power operated drive system, such as a distal portion of the elongate drive member (e.g., drive shaft). In some instances, the elongate drive shaft can be considered part of the power operated drive system because power can be utilized to cause a drive system to operate the drive shaft. Also, the drive shaft can be configured for mating and operating with mechanical components of the drive system. A portion of the drive shaft can be received into the drive system (e.g., received into the handle where the motor, transmission, or other drive components are located); however, the drive shaft can also include a portion that is contained within the sheath. The drive shaft is configured for transferring power from the drive system to the closure element during the medical procedure for closing the hole in the blood vessel.

Accordingly, the drive shaft can be part of the drive system by virtue of being the component that operates to drive a drive collar and/or closure element. As such, the sheath can have a lumen disposed around and containing at least a portion of a drive shaft, the drive collar, and the closure element. In one configuration, the drive shaft can be operably coupled with the drive collar which is associated with the closure element. The coupling between the drive shaft and drive system can be direct or indirect depending on the configuration of the vessel closure device and the mechanics employed to move the closure element within the sheath and deliver the closure element into the blood vessel.

Also, the sheath, and optionally the drive shaft, can have a coupling system that includes coupling components that can be actuated so as to allow for the proximal end of the sheath and drive shaft to be engaged and disengaged from the handle. For example, the sheath can have a manually actuated coupling member that operates the coupling system to couple the sheath and drive shaft with the handle and drive system of the vessel closure device. Additionally, the actuated coupling member can be manually manipulated to allow for the sheath and elongate drive shaft to be withdraw and disengaged from the handle and drive system. The coupling/disengaging can allow for the handle to contain the power source and a majority of driver system (e.g., substantially all driver system components except the entire drive shaft). Additionally, the sheath can be configured with a distal end that releases the closure element from the drive collar and into the wall of the body lumen. While the vessel closure device is described with the sheath and drive shaft extending into the handle when coupled together, the handle and drive system can extend into the sheath for coupling with the sheath and drive shaft. Thus, the coupling system can be reversed for the coupling mechanisms to be on the handle and/or drive system rather than on the sheath, and embodiments described herein can be reversed so that the coupling occurs at the sheath side of the device.

In one embodiment, the vessel closure device can include a handle that contains the power source, the mechanical drive system, and a proximal end of the sheath, when coupled together, such that the mechanical drive system is operably coupled to a drive collar configured to deliver the closure element from the sheath. The handle can be comprised of a primary handle portion and a secondary handle portion that are removably couplable together so as to be fluid tight when coupled together. An o-ring or other sealing member can be used to provide fluid-tightness to the handle at the coupling junction between the primary and secondary handle portions. Also, the primary handle portion can contain the mechanical drive system and the proximal end of the garage, and the secondary handle portion contains the power source, or vise versa.

In one embodiment, a power driven vessel closure system can be configured for closing a hole in a wall of a body lumen, such as a blood vessel. The vessel closure system can include a handle that is separate and removably couplable with a sheath that houses a closure element. Accordingly, the handle and sheath can be provided or obtained separately and then coupled together for use in the medical procedure. The handle can be configured to contain the components that operate the device, while the sheath can be configured to contain disposable components and components that are delivered into the body. Thus, the vessel closure device includes the connected handle and sheath, while the vessel closure system includes the handle and sheath whether connected or disconnected.

The vessel closure system can include a power source, a drive system, an elongate drive member, a drive collar, and a closure element. The handle can contain the power source and the driver system which can be operably coupled with the power source. The power source can be coupled or decoupled from the drive system. The elongate drive member, drive collar, closure element and other components can be configured and arranged as described herein.

In one embodiment, a vessel closure system can include a control member, such as a button, disposed on the handle and being configured for manual actuation to operate the drive system. Accordingly, manual actuation of the control member provides power from the power source to the drive system so as to operate the elongate drive member and translocate the drive collar and/or closure element from a proximal position to a terminal distal position or deployment position. When in the terminal distal position, the drive collar can release the closure element into the wall of the body lumen so that the closure element converts to the closed orientation and closes the hole in the wall of the body lumen.

In one embodiment, the vessel closure system can include a protective device that is configured to protect the vessel closure device (e.g., handle and sheath). The protective device can be a flexible or rigid container having an internal chamber that is configured to receive the handle and at least a proximal end of the sheath and elongate drive member such that a distal end of the sheath and elongate drive member extends out from the internal chamber. The protective device can include an openable sealing mechanism that is configured to open to receive the handle and to close and provide a fluid-tight seal. Additionally, the protective device can include an aperture opposite of the openable sealing mechanism, said aperture configured to receive a proximal end of a sheath therethrough so as to provide a fluid-tight seal with the sheath with a distal end of the sheath extending from the protective device.

In one embodiment, the present invention can include a method for closing a hole in a blood vessel with a vessel closure device as described herein. Accordingly, the method can include actuating a control member (e.g., button) so as to cause electric power (e.g., from a power source) to operate a mechanical driver system (e.g., motors, pumps, compressors, etc.) to move a closure element in a distal direction until tines (e.g., sharp points) of the closure element penetrate the blood vessel or other lumen proximal to the hole. After the closure element penetrates the blood vessel it can be released from the garage/sheath so that the closure element can convert in shape from a storage orientation (e.g., substantially tubular) to a closed orientation (e.g., substantially planar) which closes the hole by pulling portions of the blood vessel surrounding the hole together.

In one embodiment, the method of closing a hole in a blood vessel can also include inserting a distal end of a sheath that contains the closure element through the skin, and positioning a distal end of the sheath at the hole in the vessel. After the distal end of the sheath is in position, the control member can be actuated to deliver the closure element. For example, the control member can be a button, and actuating the control member can include pressing the button to move the closure element in the distal direction so as to close the hole in the blood vessel. The button can be released after the closure element has closed the hole.

In one embodiment, the method can also include performing a diagnostic protocol to ensure the device is in a status that is sufficient for delivering the closure element. For example, the vessel closure device can be run through a diagnostic protocol to determine whether an electrical power source has sufficient power to move the closure element in the distal direction and close the hole in the blood vessel. Other diagnostic protocols can be run to test one or more of the following: coupling of the handle and sheath; status of the drive system; coupling of the drive shaft with the mechanical drive system; sealed handle; fluid-tightness; position of the closure element; and other diagnostics. The diagnostic protocol can cause an indicator on the device to provide a first indication when the device is in condition to use, and a second indication when the device is not in a condition to use; however, the indicator can be configured to provide a suitable indication regarding the status of the device. For example, when the power source has sufficient power a first indication (e.g., green light, selected flash pattern, or screen data) and to provide a second indication (e.g., red light, selected flash pattern, or screen data) when the power source does not have sufficient power. The indicator can be visual or audio. Diagnostics can be performed prior, during or after delivery of the closure element, and can be performed real time during a medical procedure to provide on-the-fly diagnostic information.

During use of the device in the method for closing a hole in a blood vessel, the operator can actuate the control member so as to cause a power source to provide power to a driver system that operates an elongate drive member that drives the closure element in a distal direction. The closure element can be retained in a garage in a storage orientation (e.g., tubular) and converted to a closed orientation (e.g., planar) when released from the garage into the blood vessel so as to close the hole. Prior to use, the closure element can be retained on a drive collar in the garage, where the drive collar is coupled with the elongate drive member and the drive collar releases the closure element from the garage when reaching a terminal position within the garage. Alternatively, the closure element can have a surface configured for engaging with the drive shaft such that operation (e.g., rotation or distal translation) of the drive shaft moves the closure element in the distal direction.

In one embodiment, the method can include placing the handle of the vessel closure device within a protective device in order to protect at least the handle from body fluids. The positioning within the protective device can include the proximal end of the sheath of the vessel closure device being located within the protection device with the medial and distal portions of the sheath extending through an aperture of the protective device so as to allow the distal end of the sheath to be inserted into a body. After placement, the protective device can be sealed with the handle disposed therein so as to provide a fluid-tight seal with the sheath extending from the protective device.

In one embodiment, the method can include coupling a sheath to a handle before use. The handle is configured for being capable of being reused, and the sheath is disposable. As such, these separate components can be obtained separately and then coupled together. After completion of the medical procedure, the handle and sheath can be decoupled.

In one embodiment, the handle can include the control member, a power source, the mechanical driver system, and a proximal end of an elongate drive member. As such, the elongate drive member can be operably coupled to the driver system, and can be coupled to a drive collar that drives the closure element in the distal direction. The sheath can include a major portion of the elongate drive member, the drive collar, and the closure element disposed on the drive collar and/or elongate drive member.

After the medical procedure has been finished, the method can include removing the sheath from the handle after the hole has been closed with the closure element. Also, the method can include removing the handle from a protective device, when such a protective device is utilized to protect the handle. Additionally, the method can include disposing of the sheath as waste when the sheath and its components are configured to be disposable after a single use. Also, the handle can be sanitized prior to reuse.

II. Vessel Closure Device

The medical device is described herein in connection to various embodiments illustrated in the figures, and described to have many identical or similar structures that perform identical or similar functions. Accordingly, the description herein of embodiments of vessel closure devices and associated components should be considered in view of the other descriptions of other embodiments. Furthermore, those of ordinary skill in the art will appreciate that one or more of the components and/or features of the vessel closure device shown in one figure or embodiment may also be incorporated in another figures or embodiments.

The medical device of the present invention can be configured to repair a blood vessel or other body lumen by applying a closure element to vessel tissue adjacent to or around an opening in a blood vessel. Accordingly, the medical device of the present invention can be configured such that the vessel closure device can deliver an embodiment of a closure element to repair the blood vessel as described in connection to FIGS. 1A to 13C.

FIG. 1A illustrates an embodiment of a vessel closure device 10. The vessel closure device 10 includes a handle 12. The handle 12 is formed from a primary housing 13 (i.e., distal housing) and a secondary housing 26 (i.e., proximal housing) that cooperate to form a housing for internal components that operate the vessel closure device 10. The primary housing 13 includes a proximal end 14 (e.g., at proximal side) and an opposite distal end 16 (e.g., at distal side), where proximal and distal are relative to the mode of operation of the vessel closure device 10. For example, during use of the vessel closure device 10, the proximal end 14 of the primary housing 13 is directed away from a patient while the distal end 16 of the primary housing 13 is directed toward the patient. The proximal end 14 is directed toward the operator of the vessel closure device 10. The proximal end 14 of the primary housing 13 includes a coupling member 18 that is configured for receiving and coupling with the secondary housing 26. The distal end 16 of the primary housing 13 includes a distal opening 20 that is configured for receiving and coupling with a closure element housing 50 (e.g., sheath). Additionally, the handle 12 includes a button pad 22 (e.g., control member) that can be actuated by an operator in order to utilize the vessel closure device 10. While only one button is shown for the button pad 22, multiple buttons can be used for different functions. Also, the button pad 22 or other control member can be located on any aspect or orientation with respect to the handle 12, and the button pad 22 can also be disposed on the primary housing 13 and/or secondary housing 26.

The secondary housing 26 includes a proximal end 30 and an opposite distal end 28. An indicator 34 is shown to be disposed on the proximal end 30 of the secondary housing 26. The indicator 34 can be device that is capable of providing information to the operator of the vessel closure device 10. For example, the indicator 34 can be as simple as a light (e.g., LED) or a screen that provides real-time data, status, and the like. The distal end 28 of the secondary housing 26 includes a coupling member 32 that is configured for receiving and coupling with the primary housing 13. As shown, the coupling member 32 of the secondary housing 26 is configured to couple with the coupling member 18 of the primary housing 13. The coupling members 18, 32 can be configured in any manner that allows the secondary housing 26 to be removably coupled to the primary housing 13 so as to form the handle 12. For example, the coupling members 18, 32 can be or form a threaded coupling, a snap coupling, friction coupling, or the like. A sealing member 24 is shown to be disposed at the junction between the coupling member 32 of the secondary housing 26 and the coupling member 18 of the handle 12. The sealing member 24 can seal the handle 12 so as to be fluid tight, water resistant, and/or water proof. The sealing of the handle 12 with the sealing member 24 can protect the integrity of the components disposed therein. Examples of a sealing member 24 can include an o-ring, rubber ring, fluid-tight joint, sleeve, or the like.

As described, the distal end 16 of the primary housing 13 includes a distal opening 20 that is configured for receiving and coupling with a coupling member 52 of the closure element housing 50. Also, the closure element housing 50 can be referred to as a sheath 50 because it functions as a protective covering for the closure element and can be configured into a tubular structure. The sheath 50 can include the coupling member 52 at a proximal end 54, which is opposite of a distal end 56 that includes a distal opening 58. The distal opening 58 on the distal end 56 of the sheath 50 can be fluidly coupled with an internal lumen of the sheath 50. As shown, the sheath 50 can include a coupling mechanism 60 that is configured to allow the sheath 50 to be coupled to and removed from the handle 12. As such, the coupling mechanism 60 can cooperate with the sheath coupling member 52 of the sheath 50 and the distal opening of the primary housing 13 to facilitate coupling and decoupling of the sheath 50 with the handle 12.

FIG. 1B illustrates an embodiment of the internal components of the vessel closure device 10 illustrated and described in connection with FIG. 1A. The primary housing 13 can include a primary mating member 38 that cooperates with a secondary mating member 36 of the secondary housing 26 so as to couple the housings 13, 26 together to form the handle. The mating members 36, 38 can be present in various configurations that allows the secondary housing 26 to be removably couplable with the primary housing 13. For example, mating members 26, 28 can include features of the coupling members 18, 32, and thereby can be or form a threaded coupling, a snap coupling, friction coupling, or the like.

The primary housing 13 is shown to include the button pad 22 that operates the function of the vessel closure device 10. The button pad 22 can be in operable communication with a controller 86 that can receive input data from the button pad 22 and provide controlling data and/or power to various components. The controller 86 can be separate from or integrated with the button pad 22, such that activation of the button pad 22 can directly send control data and/or power to the various components. The data received from the button pad 22 can include activation and/or deactivation data that is then routed to various components for activation or deactivation. Also, the button pad 22 can be a complex input system, such as a keyboard, touchpad, or the like, that includes the ability to provide more complex data (e.g., activation rates, speeds, etc) and/or power to the various components. The data and/or power can be routed from the controller 86 through line 84 to a motor 78 that functions to deliver the closure element from the sheath 50. The line 84 can also be configured to provide data and/or power to the motor 78 from the controller 86, and line 84 can be one or more cables (e.g., optical and/or electronic) with one or more transfer lines disposed therein.

Optionally, motor 78 can be more than one motor, where the different motors can operate different components of the device. For example, one motor can be operably coupled to a locator assembly, as described below, such that the motor can deploy the locator assembly, and then retract the locator assembly as the closure element is being deployed.

The secondary housing 26 can include a power source 90 disposed therein. The power source 90 can be a battery or a device that is configured to be plugged into an external power source, such as a wall power outlet. The power source 90 can provide power to the controller 86 through line 88, where the controller 86 then provides power to the motor 78. Since the secondary housing 26 is decouplable from the primary housing 13, line 88 can be operably coupled to a primary connector 87 in the primary housing 13 that is removably couplable with an secondary connector 89 in the secondary housing 26. The primary connector 87 and secondary connector 89 can be configured to be plugged together so that power can be provided from the power source 90 to the controller 86. The coupled primary connector 87 and secondary connector 89 can cooperate to form a connector system 83 that is capable of transferring power and/or data between the secondary housing 26 and primary housing 13.

Additionally, the power source 90 can be operably coupled to the motor 78 through line 85. Line 85 can be configured similarly to line 88 and can be operably coupled with the connector system 83 that allows power to pass from the power source 90 to the motor 78.

The controller 86 can also be operably coupled to the indicator 34. The controller 86 can be operably coupled to the indicator 34 through line 88 and the connector system 83 so that power and/or data can pass from the controller 86 to the indicator 34. As such, the controller 86 can provide data and/or power to the indicator 34 so that the operator of the vessel closure device 10 can be notified of information related to the operation and function thereof. For example, when the indicator 34 is a light, the light can be on to identify that the device 10 is in operation or has power, and the light can be off to identify that the device 10 has no power or is off. The indicator 34 can also flash in one or more patterns to provide information to the operator. Also, multi-colored lights can be used in the indicator 34 to provide various information to the operator, where the individual colors or color combinations can provide different information. In another example, the indicator 34 can be a screen that displays information in an alphanumeric manner, which allows the operator to read the screen for information regarding the function or status of the device 10.

Additionally, the button pad 22 can be operably coupled to the indicator through like 88 and the connector system 83.

Alternatively, the button pad 22 can be integrated with the indicator 34 such that one member, such as a touch screen, can operate as both a control member and an indicator. Touch screens are well known, and can be applied to the present device.

In one instance, the indicator 34 can be a power indicator that is operably coupled to the power source 90 through line 35. The indicator 34 can then be used to notify the operator of the status of the power supply and indicate when the power supply needs to be recharged, replaced, or plugged into to an external power source.

The motor 78 is shown to be coupled with a proximal end 76 of a drive shaft 74 such that the motor 78 can operate the drive shaft 74 during a procedure to deliver the closure element 82 so as to close an opening in a vessel wall. The drive shaft 74 is also retained within an internal lumen 72 of the sheath 50. The coupling member 52 of the sheath 50 fits within the housing distal opening 20 so that the motor 78 can engage with the proximal end 76 of the drive shaft 74. Optionally, a sheath covering 70 is disposed on the sheath 50. Sheath coverings 70 can have various functions, such as providing fluid-tightness, protecting the sheath, or the like. Also, the sheath covering 70 can be removable from the sheath 50, and can be disposed or applied thereto similar to a sleeve. In another instance, the sheath covering 70 can be an introducer sheath that can receive the sheath 50 as described herein.

The sheath 50 is removably couplable with the handle 12 by the sheath coupling member 52 being capable of being received into and removed from the distal opening 20 of the primary housing 13. As shown, the coupling member 52 of the sheath 50 is received into the distal opening 20 and can be functionally coupled with a sheath coupling mechanism 60. The sheath coupling mechanism 60 can include a coupling member 62 that interacts with a primary housing coupling receiver 64 to lock the sheath 50 in place with respect to the distal opening 20 and the primary housing 13. This can include the distal opening 20 being defined by the body of the primary housing 13 so as to form the coupling receiver 64 that interacts with the coupling member 62. During insertion of the sheath 50 into the distal opening 20 or removal therefrom, the sheath coupling mechanism 60 can be depressed into the distal opening 20 so that the coupling member 62 can be disengaged from the coupling receiver 64, which allows insertion or removal.

The drive shaft 74 also includes a distal end 75, and is retained within the internal lumen 72 of the closure element housing or sheath 50. The distal end 75 of the drive shaft 74 is located adjacent to the distal opening 58 of the sheath 50, which allows for the closure element 82 to be delivered from the distal end 75 through the distal opening 58.

The closure element 82 is retained within the sheath 50 and is directly or indirectly located on the drive shaft 74, and is held in place and delivered with a drive collar 80. The drive collar 80 is positioned proximally with respect to the closure element 82 so as to be capable of distally pushing the closure element 82 for delivery to a vessel tissue. The drive collar 80 can have various configurations so as to be capable of longitudinally traversing the sheath 50 and drive shaft 74. Also, the drive collar 80 can be configured to hold the closure element 82 in a substantially tubular orientation until it reaches the distal end 75 of the drive shaft 74 and is deployed from the distal opening 58 of the sheath 50.

The sheath 50, including for example, the drive shaft 74, closure element 82, drive collar 80, can be disposable. This allows the closure device 10 to be used multiple times in a procedure. In effect, the sheath 50 can be preloaded with a closure element. For procedures where more than one opening is to be closed, the device 10 can be used by simply replacing the sheath 50 with another sheath. For example, the first sheath can be used to close an opening in a vessel wall after deployment of a stent. The first sheath can then be removed from the handle and replaced with a second sheath with a loaded closure element. The second sheath can then be used to close another opening in a body lumen or tissue. In this manner, the sheath 50 (along with the drive shaft 74, drive collar 80, etc.) becomes a disposable portion of the closure device and allows the device to be reloaded and reused in a single procedure.

FIG. 1C illustrates an embodiment of an ergonomic handle 12*a* for a vessel closure device 10. The ergonomic handle 12*a* is shown to have an ergonomic surface 92*a* for receiving the fingers of the operator of the device 10. Also, the handle 12*a* includes a flatter thumb surface 93*a* compared to the embodiment shown in FIG. 1A. The button pad 22 is shown to be positioned so as to be capable of being operated by a thumb. The device 10 is also shown to have an ergonomic handle 12*a* that is a unitary piece as opposed to a primary and secondary housing as shown in FIG. 1A; however, the handle 12*a* can be modular and couplable. The handle 12*a* also is shown to include a plug receptacle 94 that is configured to receive a power supply from an external source; wherein the plug receptacle 94 can provide electricity to the power source 90 of FIG. 1B, or can be the primary power source in a battery-less device 10. The handle 12*a* can also include a battery receptacle 37 that is configured similarly as other battery receptacles in other battery powered devices. While not specifically shown, the battery receptacle 37 can include a removable covering, a receptacle for rechargeable or standard batteries (e.g., AA, C, D, etc.), and electronics for receiving and/or providing power to or from the batteries. The indicator 34 is shown to be in a more distal position and is shaped and configured to be a readout screen. Additionally, the handle 12*a* can be configured at a right-handed, left-handed, or ambidextrous handle. Additionally, the handle 12*a* can include a component 39, which can be any of various components described herein or elsewhere for use in medical devices, electronic devices, vessel closure devices, or the like. The component 39 may include haptic feedback vibration components, acoustic alarms, memory, radio frequency receivers and/or transmitters, or the like or any combination thereof.

FIG. 2A shows the front view and FIG. 2B shows a cutaway side view of an embodiment of the handle 12 of a vessel closure device 10 so that the coupling recess 20 is viewable. These views cooperate to provide an illustration of the mechanism for inserting and coupling the distal end 65 of the sheath 50 with the handle 12. For orientation, the handle 12 is positioned so that the button pad 22 is located at the top part of the handle 12 with the distal end 16 pointing outward from the page. The coupling recess 20 is configured and shaped as a sheath receiver 40 so as to receive the sheath coupling member 52 therein. Optionally, the sheath receiver 40 can be shaped to accommodate a sheath 50 that has a sheath cover 70. As such, the sheath receiver 40 is defined by a receiver wall 44 that can have various configurations for receiving and releasing the sheath coupling member 52. The receiver 40 is also shown to have notch 42 that is shaped to receive and release the sheath coupling mechanism 60.

The sheath 50 can be coupled with the handle 12 by inserting the distal end 65 into the receiver 40 by performing one or more of the following: actuating the sheath coupling mechanism 60 for insertion into the receiver 40; pressing the sheath coupling mechanism 60 so that the sheath coupling member 62 is positioned to be capable of being inserted into the receiver 40 and/or receiver notch 42; positioning the sheath 50 within the receiver 40 such that the distal end 76 of the drive shaft 74 is operably coupled with the motor 78; engaging the drive shaft 74 with the motor 78 or motor components, transmission or the like; sliding the sheath 50 or sheath cover 70 against the receiver wall 44 until the drive shaft 74 is in an operable position; actuating the sheath coupling mechanism 60 so as to engage the receiver wall 44 or the coupling receiver 64 of the handle 12 housing or body; releasing the coupling mechanism 60 such that the sheath coupling member 62 engages the coupling receiver 64; or other similar steps or actions.

The sheath 50 can be decoupled or withdrawn from the handle 12 by performing one or more of the following: actuating the sheath coupling mechanism 60 for withdrawal from the receiver 40; pressing the sheath coupling mechanism 60 so that the sheath coupling member 62 is positioned to be capable of being withdrawn from the receiver 40 and/or receiver notch 42; releasing the sheath 50 from the receiver 40 such that the distal end 76 of the drive shaft 74 is not coupled with the motor 78; disengaging the drive shaft 74 from the motor 78 or motor components, transmission or the like; sliding the sheath 50 or sheath cover 70 against the receiver wall 44 until the drive shaft 74 is withdrawn from the receiver 40; actuating the sheath coupling mechanism 60 so as to disengage from the receiver wall 44 or the coupling receiver 64 of the handle 12 housing or body; releasing the coupling mechanism 60 such that the sheath coupling member 62 disengages from the coupling receiver 64; or other similar steps or actions.

The sheath coupling mechanism 60 can have various configurations in order to be capable of coupling the sheath 50 to the handle 12. As shown in FIG. 2B, the sheath coupling mechanism 60 can include a recess 68 that is shaped and configured for receiving the sheath coupling mechanism 60. For example, the recess 68 provides a cavity for retaining the coupling mechanism 60 and any components thereof, and provides a space to receive the coupling mechanism 60 when it is actuated for coupling/decoupling the sheath 50 and handle 12.

Optionally, the recess 68 can include a biasing member 69 that is has the coupling mechanism 60 disposed thereon. The biasing member 69 can be compressed during coupling/decoupling, and then can spontaneously return to shape and push the coupling mechanism 60 back out of the recess 68. The biasing member can be shape memory foam, rubber, elastomer, a spring, pressure bladder, or the like.

FIG. 3A shows the front view and FIG. 3B shows a cutaway side view of an embodiment of the handle 12 of a vessel closure device 10 so that the threaded coupling recess 20 is viewable. For orientation, the handle 12 is positioned so that the button pad 22 is located at the top part of the handle 12 with the distal end 16 pointing outward from the page. The coupling recess 20 is configured and shaped as a threaded sheath receiver 40 so as to receive the sheath coupling member 52 therein. As such, the threaded sheath receiver 40 is defined by a threaded receiver wall 44 having threads 46 (dashed line) that can have various configurations for receiving and releasing a threaded sheath coupling member 52. The threads 46 of the threaded receiver wall 44 can be configured to thread with threads 53 disposed on the sheath 50. Optionally, the threaded sheath receiver 40 can be shaped to accommodate a sheath 50 that has a threaded sheath cover 70, otherwise, the sheath cover 70 can proximally terminate distally from the threads.

The sheath 50 can be coupled with the handle 12 by performing one or more of the following: inserting the threads 53 of the sheath 50 into the threads 46 of the threaded receiving wall 44 of the receiver; threading the threads 53 of the sheath 50 with the threads 46 of the receiver; screwing the sheath 50 into the receiver 40; positioning the sheath 50 within the receiver 40 such that the distal end 76 of the drive shaft 74 is operably coupled with the motor 78; engaging the drive shaft 74 with the motor 78 or motor components, transmission or the like; rotating the threads 53 sheath 50 or sheath cover 70 against the threads 46 of the receiver wall 44 until the drive shaft 74 is in an operable position; or other similar steps or actions. The sheath 50 can be decoupled or removed from the handle 12 be reversing any of the aforementioned actions or unscrewing the sheath 50 from the handle 12.

FIG. 4A shows the front view and FIG. 4B shows a cutaway side view of an embodiment of the handle 12 of a vessel closure device 10 so that the coupling recess 20 is viewable. For orientation, the handle 12 is positioned so that the button pad 22 is located at the top part of the handle 12 with the distal end 16 pointing outward from the page. The coupling recess 20 is configured and shaped as a sheath receiver 40 so as to receive the sheath coupling member 52 therein. The sheath receiver 40 is defined by a receiver wall 44 that can have various configurations for receiving and releasing the sheath coupling member 52. The receiver 40 is also shown to have two oppositely disposed notches 42 that are shaped to receive and release two twist-lock tabs 49 disposed on the sheath 50 which operate as a coupling mechanism. The receiver 40 also includes two oppositely disposed twist-lock receiver slots 48. As shown in FIG. 4A, the twist-lock receiver slots 48 are about 90 degrees from the two notches 42. This allows the twist-lock tabs 49 of the sheath 50 to be inserted into the two notches 42, and then rotated about 90 degrees so that the two twist-lock tabs 49 are positioned within the two twist-lock receiver slots 48. However, the twist-lock receiver slots 48 can be at any angle with respect to the notches 42, such as 45 degrees, 60 degrees, 80 degrees, or any degree therebetween.

The sheath 50 can be coupled with the handle 12 by inserting the distal end 65 of the drive shaft 74 into the receiver 40 by performing one or more of the following: inserting the twist-lock tabs 49 of the sheath 50 into the notches 42 of the receiving wall 44 of the receiver 40; twisting the twist-lock tabs 49 with respect to the receiving wall 44 of the receiver 40 until the twist-lock tabs 49 are disposed within the twist-lock receiver slots 48; positioning the sheath 50 within the receiver 40 such that the distal end 76 of the drive shaft 74 is operably coupled with the motor 78; engaging the drive shaft 74 with the motor 78 or motor components, transmission or the like; or other similar steps or actions. The sheath 50 can be decoupled or removed from the handle 12 by reversing any of the aforementioned actions or twisting the sheath 50 so that the twist-lock tabs 49 disengage from the twist-lock slots 48 and align with the notches 42.

FIG. 5A shows a cutaway side view and FIG. 5B shows a cutaway frontal view that cooperate to illustrate internal components of an embodiment of a vessel closure device 100. As illustrated, some components are located within the handle 12 (FIG. 1A), such as the button pad 144, controller 146, power source 140, data/power lines 142, 148, and motor system 130, where the handle 12 can be configured as described herein. As described above, the power source 140 is coupled with a data/power line 142 that communicates with the controller 146. The controller 146 can receive power from the power source 140 and then provide power to the motor system 130 via the data/power line 148 in accordance with data instructions received from the button pad 144. For example, the button pad 144 can be manipulated by an operator of the device 100 in order to provide instruction data to the controller 146 that causes power to be transferred from the power source 140 to the motor system 130 for operation of the device 10. The motor system 130 can include an electric motor, transmission gearing, electronic controllers, a printed circuit board (PCB) with electronics, and any other components that can be utilized with a motorized device.

The motor system 130 is also coupled with a drive shaft 118, which can also be configured as a worm gear with respect to the drive collar 150 and closure device 170. The drive shaft 118 can have drive shaft coupling 120 that interacts and mates with a motor coupling 132. As shown, the drive shaft coupling 120 is received into the motor coupling 132 in a male/female orientation; however, the orientation can be switched so that the motor coupling 132 is received into the drive shaft coupling 120. The drive shaft coupling 120 and motor coupling 132 can have complementary gearing that interacts for a gearing system capable of transferring power from the motor system 130 to the drive shaft 118. Also, the drive shaft coupling 120 and motor coupling 132 can be configured similarly to the components that allow a drill to receive a drill bit.

The drive shaft 118 extends from the motor system 130 and into the sheath 102, which is a housing for the closure element 170. The drive shaft 118 can include an internal lumen 162, an external surface 117, and threads 116. The sheath 102 is defined by a sheath body 104 that is shaped similar to a tube having a proximal end 108 and a distal end 106. The sheath 102 also has an internal lumen 112 that opens at a distal opening 110. The proximal end 108 of the sheath 102 can include an end cap 114 having an aperture 115 for receiving the drive shaft 118 therethrough. The end cap 114 and corresponding aperture 115 can cooperate to allow the drive shaft 118 to pass from the internal lumen 112 so as to be capable of coupling with the motor system 130. Also, the end cap 114 can be shaped and configured to provide a fluid-tight seal with regard to the sheath 102 and internal lumen 112, and also provide for free rotation of the drive shaft 118.

Optionally, the sheath 102 can be covered with a sheath cover 160 or outer sheath. The sheath cover 160 can be removable from the sheath 102, and optionally disposable. The sheath cover 160 can be configured to a sleeve that slips over the sheath 150 or it can include an openable seam (not shown), such as a zipper, Velcro, ziplock, or the like, that allows the sheath cover to be opened up for receiving the sheath 102. Also, the sheath cover 160 can be an introducer sheath.

In another option, the sheath 102 and/or sheath cover 160 can include a distal end cover 122. The distal end cover 122 can seal the distal opening 110 and the internal lumen 112 so that body fluids do not enter into the internal lumen 112. The distal end cover 122 can include one or more perforations 124 (e.g., partial perforations that do not traverse through the cover 122) or other features that can be penetrated, biased, or impacted so as to open the cover 122. The distal end cover 122 can be configured to be automatically resealabe so that an object, such as a guide wire, can be passed therethrough and through the internal lumen 112 while retaining the fluid-tight seal. Various rubber stoppers or sealing caps used to retain a fluid in a container that allow for a needle to be passed through to retrieve the fluid while retaining a fluid-tight seal can be adapted for use in the end cover 122.

The lumen 112 of the sheath 102 is configured for retaining the drive collar 150 and the closure element 170. The drive collar 150 includes a threaded lumen 151 that cooperates with the threads 116 of the drive shaft 118 in order to propel the drive collar 150 distally or proximally depending on the direction of rotation of the drive shaft 118. The treads 116 of the drive shaft 118 and threaded lumen 151 of the drive collar 150 can be configured as a worm gear system, and the number of thread turns can be adjusted depending on the motor system 130 as well as the needs for deploying the closure element into a vessel. Tighter threading delivers the closure element 170 at a slower rate but with more force to penetrate the vessel, and looser threading delivers the closure element 170 at a faster rate but with less force to penetrate the vessel. This allows for threading optimization.

The drive collar 150 is shown as an embodiment that "floats" within the lumen 112 without the body of the drive collar 150 sliding against the internal surface 103 of the sheath 102. As such, the drive collar 150 has at least two oppositely disposed collar stabilizers 152. The collar stabilizers 152 can be configured to guide and stabilize the collar within the lumen 112 with respect to the internal surface 103. While only two collar stabilizers 152 are depicted, any number, such as 3, 4, 5, or more collar stabilizers can be utilized that are substantially equally spread around the drive collar 150 for internal positioning with respect to the lumen 112 and internal surface 103.

Also, the drive collar 150 is shown to have an optional collar stabilizer guide 154 that cooperates with a guide channel 158 that is optionally disposed in the internal surface 103 of the sheath 102. The collar stabilizer guide 154 can be integrated with the collar stabilizer 152 or it can be a removably couplable member attached thereto. The guide channel 158 can be configured as an elongated recess that receives the collar stabilizer guide 154 and directs the longitudinal of the collar stabilizer guide 154 and thereby the drive collar 150.

Additionally, the drive collar 150 is shown to have an optional sheath blade 156 that is configured to cut the sheath cover 160 when included on the sheath 102. The sheath blade 156 can be integrated with the collar stabilizer 152 and guide 154, or it can be a removably couplable member attached thereto. The sheath blade 156 can cut through the sheath cover 160 from the proximal to distal end as the drive collar 150 is moved distally through the lumen 112 of the sheath 102. Optionally, the sheath cover 160 can include a longitudinal perforation 164 or other configuration that allows the sheath cover 160 to be easily slit by the sheath blade 156. The longitudinal perforation 164 can act as a longitudinal guide. Also, the sheath blade 156 can be used to cut the sheath 102 so that the sheath 102 can be withdrawn after the closure element is deployed. As such, each collar stabilizer 152, guide 154, and sheath blade 156 can be a unitary blade for cutting the sheath 102, as is performed with other devices that deliver closure elements for closing an opening in a body lumen.

The distal end 106 of the lumen 112 can include stoppers 166 that are configured for stopping the distal movement of the drive collar 150. The stoppers 166 can be included at any number, while 2 are shown, such as 1 annular stopper or 3 or more stoppers placed around the internal surface 103 of the sheath 102. The stoppers 166 can be made of various materials so as to function to stop the distal movement of the drive collar 150 so that the closure element 170 can be deployed.

FIGS. 5C-5E illustrate different embodiments of the drive collar 150 in association with the internal surface 103 of the sheath 102 and with the closure element 170. The drive collar 150 can have various configurations in order to accomplish the function of (1) moving the closure element 170 distally along the longitudinal axis of the sheath 102 internal lumen 112. As such, the drive collar 150 can have a pusher surface 153 that is configured to push the closure element 170.

FIG. 5C shows an embodiment of a drive collar 150 that has the same dimensions as the internal surface 103 of the internal lumen 112. As such, the drive collar 150, pusher surface 153, and closure element contact the internal surface 103 of the sheath 102. The pusher surface 153 is substantially flat and can distally push the closure element 150 through the lumen 112.

FIG. 5D shows another embodiment of a drive collar 150a that has the same dimensions at the internal lumen 112. As such, the drive collar 150a contacts the internal surface 103 of the sheath 102. The pusher surface 153a is shown to form a recess with side surface 153b. The pusher surface 153a and side surface 153b cooperate to provide support to the closure element 170, and hold the closure element 170 away from the internal surface 103 of the sheath 102.

FIG. 5E shows another embodiment of a drive collar 150b that has the same dimensions at the internal lumen 112. As such, the drive collar 150b contacts the internal surface 103 of the sheath 102. The pusher surface 153c is an annular surface that conforms with the annular closure element 170. The pusher surface 153c cooperates with the side surface 153d to form an annular pusher recess in the shape of a ring. The pusher surface 153c and side surface 153d cooperate to provide support to the closure element 170, and hold the closure element 170 away from the internal surface 103 of the sheath 102 as well as away from the drive shaft 118.

In another embodiment, the closure element 170 can be disposed on the drive shaft 118 without a drive collar 150. As such, the closure element 170 can be configured to have a surface with threads or the like that can cooperate with the drive shaft 118 for distally deploying the closure element 170.

FIGS. 6A-6D are schematic representations illustrating a method for closing an opening 198 in a body vessel 194 with the vessel closure device 100 of FIGS. 5A-5B. FIG. 6A shows an optional method of positioning the vessel closure device 100 at the opening 198 of the body vessel 194. As shown, a guide wire 180 is disposed within the lumen 196 of the body vessel 194, such as from another medical procedure that utilized an arteriotomy. A sheath cover 160 (e.g., introducer sheath) configured as a guide can be used to pass the guide wire 180 through an internal lumen so that the sheath cover 160 is disposed at the opening 198 of the vessel 194. As such, the sheath cover 160 can pass through the skin 190 and tissue 192 before being placed at the opening 198 of the vessel 194, and forming a tissue tract 197 for receiving the vessel closure device 100. This allows the sheath cover 160 in the form of a shaped tube to be used with a guide wire 180 for placement adjacent to the opening 198.

The vessel closure device 100 can be placed at the opening 198 of the vessel 194 by use of the sheath cover 160 as a guide and a guide wire 180; however, the vessel closure device can also be placed at the opening without the use of the sheath cover 160 and guide wire 180. Since the sheath cover 160 is an optional component and can be optional in the placement of the vessel closure device 100, it is shown as dashed lines to identify that it is an option. Also, the dashed lines can represent that the sheath cover 160 is an introducer sheath for introducing the sheath 102 to the blood vessel 194.

As shown in FIG. 6B, the sheath 102 of the vessel closure device 100 can be inserted through the lumen of the sheath cover 160 so as to traverse the skin 190 and tissue 192 to be placed at the opening 198 of the vessel 194. After the sheath 102 is in position, the handle (see other figures) can be actuated so as to activate the motor system (see other figures) to drive the drive collar 150 distally down the lumen 112 of the sheath 102. The collar stabilizers 152 can optionally be used to guide the drive collar 150 within the lumen 112. The drive collar 150 pushes the closure element 170 distally via the worm gear system until both elements reach the distal end of the sheath 102, lumen 112, and drive shaft 118. A stop member 166 is disposed within the lumen 112 and positioned so as to be capable of impeding the distal movement of the drive collar 150. The stop member 166 can be configured, positioned, and shaped to stop the distal movement of the drive collar 150 directly, or indirectly through stopping the distal movement of the collar stabilizers 154. More than one stop member 166 can be included.

Figure 6C:
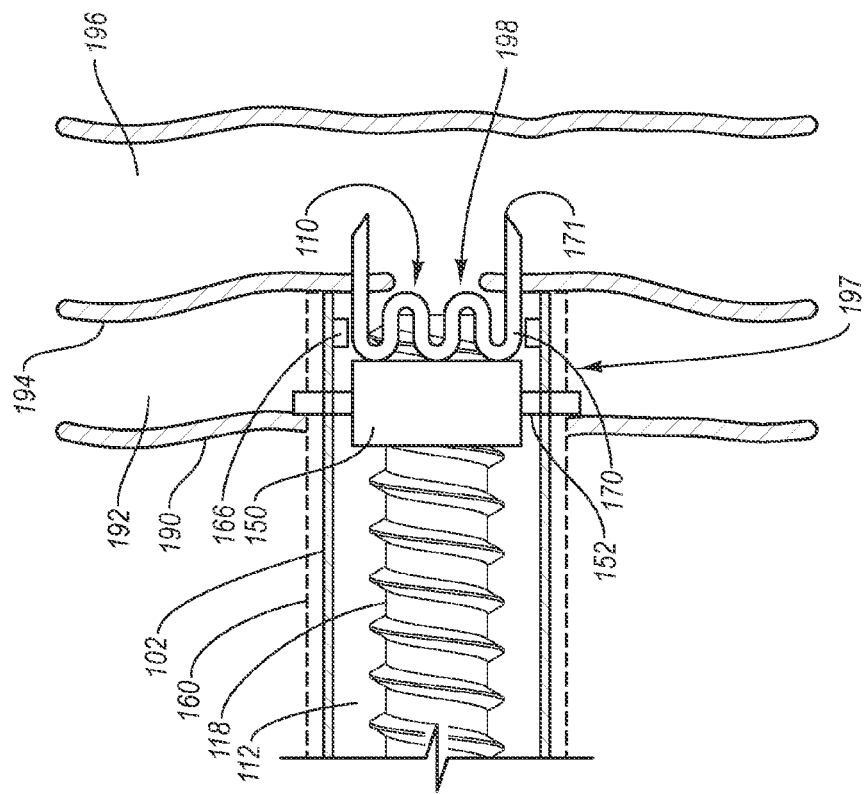

As shown in FIG. 6C, the drive collar 150 can push the closure element 170 out of the distal opening 110 of the lumen 112 of the sheath 102. As the closure element 170 is pushed out from the lumen 112, the sharp points 171 of the closure element 170 can penetrate the vessel 195 at positions outward and adjacent to the opening 198. It should be noted that the sharp points 171 of the closure element 170 can begin to penetrate the tissue while a portion of the closure element 170 is in a tubular orientation and still retained within the lumen 112.

As shown in FIG. 6D, the drive collar 150 can be stopped from moving distally by the stoppers 166, which are shown to interact with the collar stabilizer 150; however, the stoppers 166 can be configured to interact with the drive collar 150. As the drive collar 150 is stopped at the end of the lumen 112 and drive shaft 118, the closure element 170 can be released from the sheath 102. The closure element 170 can then automatically change shape so as to close and pull the vessel 194 together and close the opening 198a (closed opening). The closed opening 198a can seal the vessel 194 so that fluids within the lumen 196 do no pass through the opening 198a. After deploying the closure element 170, the device 100 can be withdrawn from the tissue tract 197 and skin 190. The tissue 192 and skin 190 can then be repaired with bandages, plugs, or the like. While not shown, the closure element 170 can have the tines 171 in an orientation as shown (e.g., about 45 degrees), or can be at any angle from 90 degrees to planar. It is possible that the tines 171 can be oriented so that the closure element is substantially planar when the opening 198a is closed.

FIG. 7A shows a cutaway side view and FIG. 7B shows a cutaway frontal view that cooperate to illustrate internal components of an embodiment of a vessel closure device 200. As illustrated, some components are located within the handle 12, such as the button pad 244, controller 246, power source 240, data/power lines 242, 248, and motor system 230, where the handle 12 can be configured as described herein. As described above, the power source 240 is coupled with a data/power line 242 that communicates with the controller 246. The controller 246 can receive power from the power source 240 and then provide power to the motor system 230 via the data/power line 248 in accordance with data instructions received from the button pad 244. For example, the button pad 244 can be manipulated by an operator of the device 200 in order to provide instruction data to the controller 246 that causes power to be transferred from the power source 240 to the motor system 230 for operation of the device 200. The motor system 230 can include an electric motor, transmission gearing, electronic controllers, a printed circuit board (PCB) with electronics, and any other components that can be utilized with a motorized device.

The motor system 230 is also coupled with a drive shaft 218, which can also be configured as a worm gear with respect to each other. The drive shaft 218 can have a drive shaft coupling 220 that interacts and mates with a motor coupling 232. As shown, the drive shaft coupling 220 is received into the motor coupling 232 with a worm gear system. The drive shaft coupling 220 and motor coupling 232 can have complementary gearing that interacts for any gearing system capable of transferring power from the motor system 230 to the drive shaft 218.

The drive shaft 218 extends from the motor system 230 and into the sheath 202, which is a housing for the closure element 270. The drive shaft 218 can include an internal lumen 262 and threads (not shown). The sheath 102 is defined by a sheath body 204 that is shaped similar to a tube having a proximal end 208 and a distal end 206. The sheath 202 also has an internal lumen 212 that opens at a distal opening 210. The proximal end 208 of the sheath 202 can include an end cap 214 having an aperture 215 for receiving the drive shaft 218 therethrough. The end cap 214 and corresponding aperture 215 can cooperate to allow the drive shaft 218 to pass from the internal lumen 212 so as to be capable of coupling with the motor system 230. Also, the end cap 214 can be shaped and configured to provide a fluid-tight seal with regard to the sheath 202 and internal lumen 212, and also provide for free rotation of the drive shaft 218.

Optionally, the sheath 202 can be covered with a sheath cover 260 or outer sheath, or a guide sheath or other tubular medical device. The sheath cover can be configured and/or used as described herein. The sheath cover 260 can receive the sheath 202 and be removable from the sheath 202, and optionally disposable. The sheath cover 260 can be configured to a rigid or flexible sleeve that slips over the sheath 202 or it can include an openable seam (not shown) to be opened up for receiving the sheath 202. Optionally, the sheath cover 260 can include a longitudinal perforation 264 or other configuration that allows the sheath cover 260 to be easily slit by the sheath blade 256. The longitudinal perforation 264 can act as a longitudinal guide.

The sheath 202 and/or sheath cover 260 can include a distal end cover 222. The distal end cover 222 can seal the distal opening 210 and the internal lumen 212 so that body fluids do not enter into the internal lumen 212. The distal end cover 222 can include one or more perforations 224 (e.g., partial perforations that do not traverse through the cover 222) or other features that can be penetrated, biased, or impacted so as to open the cover 222. The distal end cover 222 can be configured to be automatically resealabe so that an object, such as a guide wire, can be passed therethrough and through the internal lumen 212 while retaining the fluid-tight seal. The distal end cover 222 can be coated wholly or in select locations with hemostatic agent and appropriate coating for controlled drug release.

The lumen 212 of the sheath 202 is configured for retaining the drive collar 250 and the closure element 270. The drive collar 250 includes a smooth, slippery, lubricated, or otherwise slidable lumen 251 that cooperates with the smooth, slippery, lubricated, or otherwise slidable surface 217 of the carrier tube 216. The drive collar 250 can be propelled distally or proximally over the carrier tube 216 depending on the direction of the drive shaft 118. While not shown, the lumen 251 of the drive collar 250 and the surface 217 of the carrier tube 216 can have cooperating rails and slots for guiding the drive collar 250 and inhibit rotation of the drive collar 250 with respect to the sheath 202.

The drive collar 250 is shown to float within the lumen 212 without the body of the drive collar 250 sliding against the internal surface 203 of the sheath 202; however, other drive collar 250, lumen 212, and closure element 270 can be configured so that the drive collar 250 and/or closure element 270 slide along the surface of the lumen 212. As such, the drive collar 250 has at least two oppositely disposed collar stabilizers 252. Also, the drive collar 250 is shown to have an optional collar stabilizer guide 254 that cooperates with a guide channel 258 that is optionally disposed in the internal surface 203 of the sheath 202. Additionally, the drive collar 250 is shown to have an optional sheath blade 256 that is configured to cut the sheath cover 260 when included on the sheath 202. The distal end 206 of the lumen 112 can include stoppers 266 that are configured and/or used as described herein.

FIG. 7C is another embodiment of a cross-sectional profile of a drive collar 250 and carrier tube 216. As shown, the drive shaft 218 is coupled to the drive collar 250 at a coupling 255. Also, the carrier tube 216 and drive collar 250 combination is configured so that the components are slidable with respect to each other without radially rotating.

FIGS. 8A-8C are schematic representations illustrating another method for closing an opening 198 in a body vessel 194 with the vessel closure device 200 of FIGS. 7A-7B. Also, the method shown in FIGS. 8A-8C can be combined with the method of FIG. 6A. Accordingly, the vessel closure device 200 can be inserted through skin 190 and positioned at the opening 198 of the body vessel 194. A guide wire 180 can be used for positioning the vessel closure device 200 at the opening 198. The vessel closure device 200 can be placed at the opening 198 of the vessel 194 by use of the sheath cover 260 (or introducer sheath); however, the vessel closure device 200 can also be placed at the opening without the use of the sheath cover 260. Since the sheath cover 260 is an optional component and can be optional in the placement of the vessel closure device 200, it is shown as dashed lines to identify that it is an option.

As shown in FIG. 8A, the sheath 202 of the vessel closure device 200 can be inserted through the lumen of the sheath cover 260 so as to traverse the skin 190 and tissue 192 to be placed at the opening 198 of the vessel 194. After the sheath 202 is in position, the handle (see other figures) can be actuated so as to activate the motor system (see other figures) to drive the drive collar 250 and/or drive shaft 218 distally down the lumen 212 of the sheath 202. The collar stabilizers 252 can optionally be used to guide the drive collar 250 within the lumen 212. The drive collar 250 pushes the closure element 270 distally via the worm gear system (FIGS. 7A-7B) until both elements reach the distal end of the sheath 202, lumen 212, and carrier shaft 216. A stop member 266 is disposed within the lumen 212 and positioned so as to be capable of impeding the distal movement of the drive collar 250. The stop member 266 can be configured, positioned, and shaped to stop the distal movement of the drive collar 250 directly, or indirectly through stopping the distal movement of the collar stabilizers 254. More than one stop member 266 can be included.

The stop member 266 can be an actual member, or the function thereof can be obtained from selectively configuring the device 200 to stop when the drive collar 250 reaches a certain distal point. Such a configuration can be achieved through programming the device 200 to stop movement of the drive shaft 218 at a certain point, or configure the drive components to have stops that stop the distal movement. There are a myriad of device 200 configurations that can be employed. Also, the proximal end of the drive shaft 218 can have a stop member (not shown, but similar to stoppers 319 of FIG. 9A) that inhibits further distal movement of the drive collar 250.

As shown in FIG. 8B, the drive collar 250 can push the closure element 270 out of the distal opening 210 of the lumen 212 of the sheath 202. As the closure element 270 is pushed from out from the lumen 212, the sharp points 271 of the closure element 270 can penetrate the vessel 194 at positions outward and adjacent to the opening 198. It should be noted that the sharp points 271 of the closure element 270 can begin to penetrate the tissue while a portion of the closure element 270 is in a tubular orientation and still retained within the lumen 212.

As shown in FIG. 8C, the drive collar 250 can be stopped from moving distally by the stoppers 266 or by other means. The stoppers 266 are shown to interact with the collar stabilizer 250; however, the stoppers 266 can be configured to interact with the drive collar 250. As the drive collar 250 is stopped at the end of the lumen 212 and carrier shaft 216, the closure element 270 can be released from the sheath 202. The closure element 270 can then automatically change shape so as to close and pull the vessel 194 together and close the opening 198a (closed opening). The closed opening 198a can seal the vessel 194 so that fluids within the lumen 196 do no pass through the opening 198a. After deploying the closure element 270, the device 200 can be withdrawn from the tissue tract 197 and skin 190. The tissue 192 and skin 190 can then be repaired with bandages, plugs, or the like.

FIG. 9A shows a cutaway side view and FIG. 9B shows a cutaway frontal view that cooperate to illustrate internal components of an embodiment of a vessel closure device 300. As illustrated, some components are located within the handle 12, such as the button pad 344, controller 346, power source 340, data/power lines 342, 348, and drive system 315, where the handle 12 can be configured as described herein. As described above, the power source 340 is coupled with a data/power line 342 that communicates with the controller 346. The controller 346 can receive power from the power source 340 and then provide power to the drive system 315 via the data/power line 348 in accordance with data instructions received from the button pad 344. For example, the button pad 344 can be manipulated by an operator of the device 300 in order to provide instruction data to the controller 346 that causes power to be transferred from the power source 340 to the drive system 315 for operation of the device 300. The drive system 315 can include various components that can be used to deliver a closure element 370 to close an opening in a vessel. As shown, the drive system 315 can include: a drive system controller 321; a driver 320; one or more drive transmission elements 330; one or more transmission couplings 323; one or more valves 325; one or more drive shafts 318; one or more drive shaft stoppers 319; and the like.

The drive system controller 321 can be configured to receive driver instructions from the controller 346, and provide control to the movement or function of the various drive system components. Also, the drive system controller 321 can be integrated with the controller 346, or can be optional. The driver 320 can be a pump, motor, and pressure-increasing fixtures, pressurizer, compressor, or the like that can increase the pressure of a gas, such as air, oxygen, nitrogen, or the like. The drive transmission 330 can be tank, container, or the like that can receive an increase in pressure from the driver 320. The drive transmission 330 can be a tank that includes an internal pressure chamber 332 that is configured for retaining elevated pressures that are sufficient to drive the drive shafts 318 so as to deliver a closure element 370 into a vessel wall. The transmission couplings 323 can be fluid-tight fittings that couple the transmissions 330 together and/or with the driver 320. The valves 325 can be placed between each component so as to control the flow of fluid between the driver 320, transmission 330, and/or couplings 323. The one or more drive shafts 318 can be configured similarly to a plunger partially disposed in the transmission 330 such that an increase in pressure in the transmission 330 can propel the drive shafts 318 in a distal direction, whereas a reduction in pressure or creation of a vacuum therein can propel the drive shafts 318 in a proximal direction. The drive shafts 318 can each include stoppers 319 that limit the distal and/or proximal movement of the drive shafts 318. Additionally, the driver system 315 can include an electric motor, transmission gearing, electronic controllers, a printed circuit board (PCB) with electronics, and any other components that can be utilized with a motorized device or pump system.

In operation, the drive system controller 321 can receive instructions from the controller 346 so as to operate the drive system 315. The driver 320 can then cause an increase in pressure to be achieved, and the increased pressure can be transferred through the coupling 323 to the transmissions 300. The drive system controller 321 can receive and provide information, instructions, data, or the like with the controller 346.

The one or more drive shafts 318 can extend from the drive system 315 and into the lumen 312 of the sheath 302, which is a housing for the closure element 370. As shown, each drive shaft 318 is coupled to the drive collar 350 at a coupling 355.

The sheath 302 is defined by a sheath body 304 that is shaped similar to a tube having a proximal end 308 and a distal end 306. The sheath 302 also has an internal lumen 312 that opens at a distal opening 310. The proximal end 308 of the sheath 302 can include an end cap 314 having one or more apertures 317 configured for receiving the one or more drive shafts 318 therethrough. The end cap 314 and corresponding apertures 317 can cooperate to allow the drive shafts 318 to pass from the internal lumen 312 so as to be capable of coupling with the drive system 315. Also, the end cap 314 can be shaped and configured to provide a fluid-tight seal with regard to the sheath 302 and internal lumen 312, and also provide for free rotation of the drive shafts 318.

Optionally, the sheath 302 can be covered with or received into a sheath cover 360 or outer sheath, or a guide sheath or other tubular medical device. The sheath cover 360 can receive the sheath 302 and be removable from the sheath 302, and optionally disposable. The sheath cover 360 can be configured as a rigid or flexible sleeve that slips over the sheath 302 or it can include an openable seam (not shown) to be opened up for receiving the sheath 302.

The sheath 302 and/or sheath cover 360 can include a distal end cover 322. The distal end cover 322 can seal the distal opening 310 and the internal lumen 312 so that body fluids do not enter into the internal lumen 312. The distal end cover 322 can include one or more perforations 324 (e.g., partial perforations that do not traverse the cover 322) or other features that can be penetrated, biased, or impacted so as to open the cover 322. The distal end cover 322 can be configured to be automatically resealabe so that an object, such as a guide wire, can be passed therethrough and through the internal lumen 312 while retaining the fluid-tight seal. The distal end cover 322 can be coated wholly or in select locations with hemostatic agent and appropriate coating for controlled drug release.

The lumen 312 of the sheath 302 is configured for retaining the drive collar 350 and the closure element 370. The drive collar 350 includes a smooth, slippery, lubricated, or otherwise slidable lumen 351 that cooperates with the smooth, slippery, lubricated, or otherwise slidable surface 317 of the carrier tube 316. Optionally, the carrier tube 316 can be a solid carrier shaft or have an internal lumen 362 for receiving a guide wire. The drive collar 350 can be propelled distally or proximally over the carrier tube 316 depending on the direction of the drive shaft 318. While not shown, the lumen 351 of the drive collar 350 and the surface 317 of the carrier tube 316 can have cooperating rails and slots for guiding the drive collar 350 and inhibit rotation of the drive collar 350 with respect to the sheath 302.

The drive collar 350 is shown to float within the lumen 312 without the body of the drive collar 350 sliding against the internal surface 303 of the sheath 302; however, the drive collar 350, lumen 312, and closure element 370 can be configured so that the drive collar 350 and/or closure element 370 slide along the internal surface 303 of the lumen 312. As such, the drive collar 350 has at least two oppositely disposed collar stabilizers 352. Also, the drive collar 350 is shown to have an optional collar stabilizer guide 354 that cooperates with a guide channel 358 that is optionally disposed in the internal surface 303 of the sheath 302. Additionally, the drive collar 350 is shown to have an optional sheath blade 356 that is configured to cut the sheath cover 360 when included on the sheath 302.

The device 300 can be used to deploy a closure element 370 in a manner similar to FIGS. 6A-6D and/or 8A-8C. In addition, the drive system 315 can be configured to use pressure to drive the drive shaft 318 distally so that the drive collar 350 delivers the closure element 370 into a vessel wall to close an opening therein.

III. Protective Device

Figure 10A:
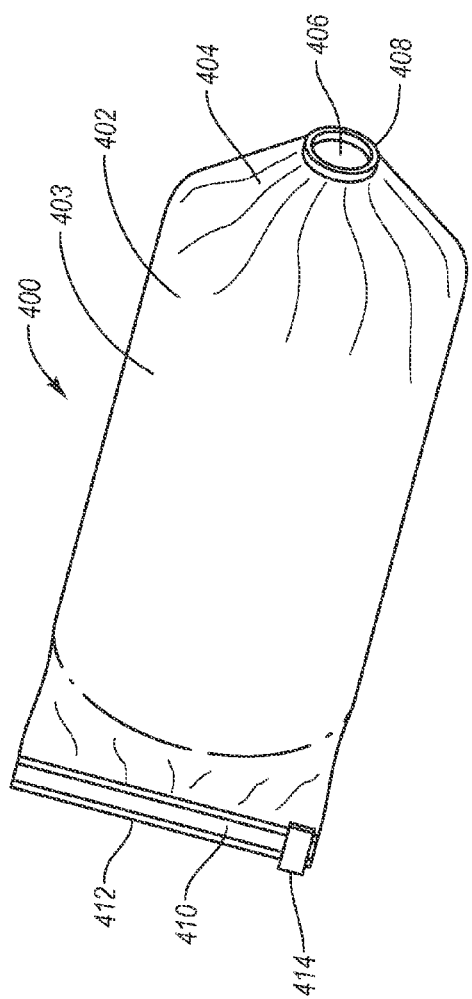
FIG. 10A is a side view illustrating an embodiment of a sanitary device for a vessel closure device.
Figure 10B:
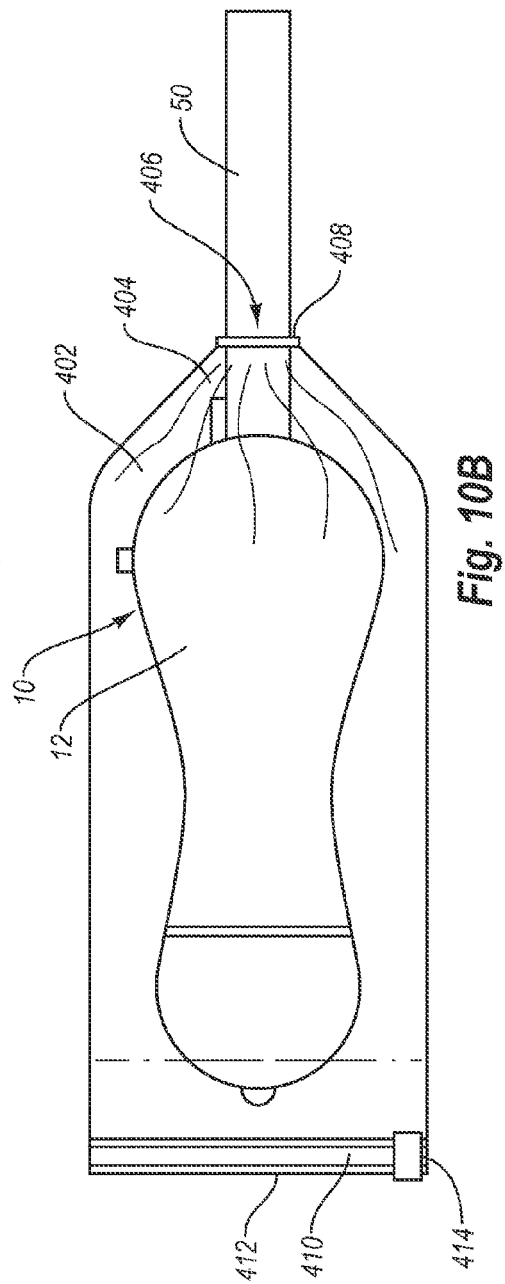
FIG. 10B is a side view illustrating a vessel closure device being disposed within the sanitary device of FIG. 10A.

FIG. 10A illustrates an embodiment of a protective device 400 that can be used to protect the vessel closure device 10. FIG. 10B shows the vessel closure device 10 being disposed within the protective device 400. For example, the protective device 400 can be used to protect the device 10 so that body fluids do not enter into the internal portion of the handle 12. The protective device 400 can be configured as a flexible or rigid bag, box, or other container that can receive the device 10 therein and provide a fluid-tight environment. As such, the device 400 can include a body 402 that defines an internal chamber 403 that receives the handle 12. The body 402 can optionally include a tapered portion 404 that conforms with the shape of the handle 12. Also, the tapered portion 404 can be used to fit the body 402 with an aperture 406 or opening that can receive the sheath 50 of the device 10. The aperture 406 can be defined by an aperture wall 408 or ring that is dimensioned to fit tightly against the sheath 50 so as to provide a fluid-tight boundary against body fluids. The aperture wall 408 can be flexible, stretchable, have shape memory, rigid, or the like. Opposite of the aperture 406, the protective device 400 can include a sealable opening 410. The sealable opening 410 can be configured in any manner that allows the opening 410 to be opened to receive the device 10, and then closed and sealed to retain the device within the chamber 403 so as to be fluid tight. However, the sealable opening 410 can be configured such that it does not provide a fluid tight seal, but can be configured to close the protective device 400. The sealable opening 410 can include a sealable member 412 and a seal actuator 414. As such, the seal actuator 414 can be actuated, moved, operated, or otherwise manipulated to open and/or close the sealable member 412. For example, the sealable member 412 and/or seal actuator 414 can be configured similar to a zip-lock sealing mechanism. Also, the seal actuator 414 can be optional when the sealable member 412 can be sealed by hand without the aid of the actuator. Alternatively, the seal member 412 and/or seal actuator 414 can be configured as any sealable system to function similarly as a zipper, Velcro, glue, adhesive, zip-cord, elastic, or the like. In fact, the sealable opening 410 can be configured to close without sealing.

IV. Closure Element

A closure element in accordance with the present invention can have a variety of shapes, sizes, and modes of operation. A star-shaped closure element or circular closure element with a central lumen and tines pointing toward the center can be configured for being disposed on a carrier member can be convenient for storage in the garage, and for being delivered into tissue for repairing an opening in a blood vessel. The closure element can be similar in form and function to closure elements used for closing incisions in blood vessels. Such a closure element can be configured to be retained within the garage in an orientation to optimize space and deployment potential and efficacy, and can be configured for automatically changing to an orientation that grabs an optimum amount of tissue before reverting to the normal or set orientation that pulls the grabbed tissue together to close the opening in the blood vessel, such as blood vessel tissue. The closure element can also be configured to flare to a larger diameter during the process of changing from the retained or delivery orientation to the orientation for penetrating and grabbing tissue. Additionally, various materials can be used for a closure element that has the functionality and characteristics as described herein. Moreover, the closure element can be coated with a polymer/drug coating so that a drug can aid in closing and sealing the opening in the blood vessel, such as a hemostatic drug. Also, a drug can be used for treating complications or infections.

FIGS. 11A-11H illustrate one embodiment of a closure element (also referred to as a "star closure element" or "star-shaped closure element") 500 in accordance with the present invention. The closure element 500 can have a generally annular-shape body 510 (shown in FIG. 11A-11B) defining a channel 540 and one or more barbs and/or tines 520 (shown in FIGS. 11A-11B) for receiving and engaging tissue adjacent or within a fistula. While only two tines 520 are shown, any number of tines can be included in the closure element. Although the closure element 500 has a natural shape and size that is set as a memory shape, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 11A-11B. The natural cross-section 530 of the closure element 500 can be reduced to form a reduced closure element 500a that has a natural, planar configuration with opposing tines 520 and a reduced cross-section 530a as shown in FIGS. 11C-11D. The closure element 500 can be expanded as shown in FIGS. 11A-11B or contracted as shown in FIGS. 11C-11D. As such, the closure element 500 can be collapsed and/or expanded depending on the situation, as provided by a shape memory material.

By rotating the opposing tines 520 axially as shown in FIG. 11E, the reduced closure element 500a can be further deformed to form a substantially tubular closure element 500b (shown by dashed lines in FIG. 11E and shown along the central axis in FIG. 11F) having the reduced cross-section 530a and aperture diameter 550 as well as being in a substantially tubular configuration with the tines 520 in an axial configuration. FIG. 11F shows a view of the closure element 500b in a storage orientation. FIG. 11G illustrates a side profile of the closure element 500b in the substantially tubular configuration, which is the storage orientation. FIG. 11H illustrates a side profile of the closure element 500c in which the body is in the substantially tubular configuration; however, the tines 521 are directed at any one of various angles from 0 degree (distally) to 180 degrees (proximally). The embodiment shown in FIG. 11H can provide for different storage and delivery orientations.

When in the storage orientation as shown in FIGS. 11F-11G, the closure element 500b can include a carrier surface 501 that is configured to contact a carrier surface of a carrier tube and/or drive shaft as described herein. The carrier surface 501 can be configured such that a drive collar is optional, and the carrier surface 501 can function as a drive collar. This can include the carrier surface 501 having threads that mate with a threaded drive shaft so that the closure element 500b and drive shaft function as a worm gear. Alternatively, the carrier surface 501 can be smooth and slippery such that the closure element 500b can slide along the surface of a carrier tube when being moved in the distal direction.

Being configured to draw the vessel tissue surrounding an opening in a blood vessel together so as to be substantially close, the closure element 500 can be formed from any suitable material, including any biodegradable material, any shape memory alloy, such as alloys of nickel-titanium, or any combination thereof. Additionally, it is contemplated that the closure element may be coated with a beneficial agent or be constructed as a composite, wherein one component of the composite would be a beneficial agent. As desired, the closure element 500 may further include radiopaque markers (not shown) or may be wholly or partially formed from a radiopaque material to facilitate observation of the closure element 500 using fluoroscopy or other imaging systems. Exemplary embodiments of a closure element are disclosed in U.S. Pat. Nos. 6,197,042, and 6,623,510, and in co-pending application Ser. Nos. 09/546,998, 09/610,238, and 10/081,726, which are expressly incorporated herein by reference.

In one embodiment, the closure element is configured to expand in an amount sufficient so that the times are capable of penetrating into the bloods vessel tissue around the opening. Accordingly, the closure element and tines are configured to expand to a maximum size and/or diameter during deployment so as to maximize the amount of tissue grabbed by the tines and drawn inward to close the opening. This can include when the closure element is applied to as shown in the FIG. 6A-6D or 8A-8C.

FIG. 12A illustrates an embodiment of a carrier tube 600 or drive shaft that has a radially-increasing taper 602 at the distal end 604. As shown, the carrier tube 600 can be employed to retain and expand the closure element upon deployment into the blood vessel. FIG. 12B shows a threaded drive shaft 610 can include a tapered member 612 at the distal end 614, which can be used at the distal end 614 of the drive shaft 610 to expand the closure element. The closure element can be dimensioned so as to be retained and/or deployed in a manner that expands and extends the tines further outwardly from the opening and/or into the tissue around the opening, which allows for more tissue to be grabbed and pulled together. The present invention provides for the closure element to expand to a diameter sufficient to close an opening in a blood vessel, such as from an arteriotomy. Since blood vessel openings can vary greatly in the diameter of the opening, the closure elements correspondingly vary so as to be capable of penetrating tissue surrounding the opening. Also, the tines can vary in size with some being larger than others. The closure element diameter and/or tines allow for more tissue to be pulled together and are suitable for closing openings without causing more trauma from larger incisions when the closure device is delivered through the skin and tissue.

In one embodiment, the closure element is configured to extend the tines further outward during deployment before turning and penetrating into the tissue. With respect to the longitudinal axis of the garage, the tines are directed radially away from the axis to form a larger and/or maximum diameter before turning and penetrating into the tissue surrounding the opening of the opening. The superelastic property of the closure element allows for such a configuration and function during deployment and closure of the opening, which can be likened to the closure element body and tines being more flat and extending perpendicularly (or angle between 45 degrees to 90 degrees) before turning inwardly to a more tubular shape, and then to the closed and natural shape with the tines pointing more inwardly. As such, the tines would make substantially a 90 degree turn during the deployment into the tissue to close the opening. This can be seen in FIG. 11H.

In one embodiment, the closure element body and/or tines (e.g., extended tines) have barbs, hooks, spikes, prongs, protrusions, roughened surfaces, and the like in order to increase the efficiency of tissue contact and grab. As such, the closure element has increased contact points for increasing the contact with the tissue during deployment.

Previous closure elements employed in closing incisions formed in blood vessels have been designed with decreased flexibility and/or increased mechanical strength due to the blood vessel being a high pressure network with blood pressure against the arterial walls. Accordingly, closure elements configured for closing an incision in a blood vessel can be configured to resist blood pressure.

In one embodiment, the closure element can be prepared from a biodegradable material. This allows for the closure element to be degraded over time after being inserted into the body to close the opening in the blood vessel. Biodegradable polymers can be formed into closure elements to have the properties described herein. The list of biocompatible polymers includes such biodegradable polymers that would be suitable for preparing a biodegradable closure element of the present invention.

In one embodiment, the closure element is coated with an active pharmaceutical ingredient with or without a polymeric carrier. The active pharmaceutical ingredient can be any drug; however, it is preferable for it to increase tissue growth The polymeric coating and drug are configured to cooperate so as to form a diffusion pathway (e.g., lipophilic, hydrophilic, and/or amphipathic) with tissue when the closure element penetrates the tissue and closes the opening in the blood vessel. This allows for the drug to preferentially diffuse into the tissue instead of into a body fluid passing over the closure element. As such, a maximum systemic blood concentration of the drug is less than or about 30 ng/ml, more preferably less than or about 20 ng/ml, and most preferably less than or about 10 ng/ml.

A biocompatible closure element or polymeric coating on the closure element can also be provided so that the closure element can be loaded with and deliver beneficial agents or drugs, such as therapeutic agents, pharmaceuticals and radiation therapies. Accordingly, the polymeric closure element and/or coating material can contain a drug or beneficial agent to improve the use of the closure element. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof. Another example of a suitable beneficial agent is described in U.S. Pat. Nos. 6,015,815 and 6,329,386 entitled "Tetrazole-containing rapamycin analogs with shortened half-lives", the entireties of which are herein incorporated by reference.

More specific examples of drugs that can be included in the coating of the closure element include any of the following: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) II$_b$/III$_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors. Also, it should be recognized that many active agents have multiple pharmaceutical uses other than those specifically recited.

The closure element of the present invention can be made of a variety of biocompatible materials, such as, but not limited to, those materials which are well known in the art of endoprostheses. Generally, the materials for the closure element can be selected according to the structural performance and biological characteristics that are desired, such as superelasticity, flexibility, size, shape, changes in orientation, biodegradability, drug elution, and the like.

In one configuration, the closure element can be made of a single material or of multiple layers, with at least one layer being applied to a primary material. This can include a metal primary material and polymer/drug topcoat or a different metal top layer. The multiple layers can be resiliently flexible materials or rigid and inflexible materials, and selected combinations thereof. For example, materials such as Ti3Al2.5V, Ti6A14V, 3-2.5Ti, 6-4Ti and platinum may be particularly good choices for adhering to a flexible material, such as, but not limited to, nitinol and providing good crack arresting properties. The use of resiliently flexible materials can provide force-absorbing characteristics, which can also be beneficial for absorbing stress and strains, which may inhibit crack formation at high stress zones. Also, the multiple layers can be useful for applying radiopaque materials. For example, types of materials that are used to make a closure element can be selected so that the closure element is capable of being in a first orientation (e.g., delivery orientation) during placement and capable of transforming to a second orientation (e.g., deploying orientation) when deployed to close the fistula.

Embodiments of the closure element can include a material made from any of a variety of known suitable biocompatible materials, such as a biocompatible shaped memory material (SMM). For example, the SMM can be shaped in a manner that allows for a delivery orientation while within the garage of the shaft of the medical device, but can automatically retain the memory shape of the closure element once deployed from the garage and into the tissue to close the fistula. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have an initial shape that can then be configured into a memory shape by heating the SMA and conforming the SMA into the desired memory shape. After the SMA is cooled, the desired memory shape can be retained. This allows for the SMA to be bent, straightened, twisted, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture. This can be used to tune the closure element so that it reverts to the memory shape to close the fistula when deployed at body temperature and when being released from the garage.

For example, the primary material of a closure element can be of a NiTi alloy that forms superelastic nitinol. In the present case, nitinol materials can be trained to remember a certain shape, retained within the garage in the shaft, and then deployed from the garage so that the tines penetrate the tissue as it returns to its trained shape and closes the fistula. Also, additional materials can be added to the nitinol depending on the desired characteristic. The alloy may be utilized having linear elastic properties or non-linear elastic properties.

An SMP is a shape-shifting plastic that can be fashioned into a closure element in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can be formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo(ε-caprolactone)diol, oligo(p-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

A closure element body having at least one layer made of an SMM or suitable superelastic material and other suitable layers can be compressed or restrained in its delivery configuration within the garage, and then deployed into the tissue so that it transforms to the trained shape and closes the fistula.

Also, the closure element can be comprised of a variety of known suitable deformable materials, including stainless steel, silver, platinum, tantalum, palladium, nickel, titanium, nitinol, nitinol having tertiary materials (U.S. 2005/0038500, which is incorporated herein by specific reference), niobium-tantalum alloy optionally doped with a tertiary material (U.S. 2004/0158309, 2007/0276488, and U.S. Ser. No. 12/070,646, which are each incorporated herein by specific reference) cobalt-chromium alloys, or other known biocompatible materials. Such biocompatible materials can include a suitable biocompatible polymer in addition to or in place of a suitable metal. The polymeric closure element can include biodegradable or bioabsorbable materials, which can be either plastically deformable or capable of being set in the deployed configuration.

In one embodiment, the closure element is made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol closure element. The nitinol closure element has improved radiopacity yet retains its superelastic and shape memory behavior and further maintains a thin body thickness for high flexibility. For example, the closure element according to the present invention has 42.8 atomic percent nickel, 49.7 atomic percent titanium, and 7.5 atomic percent platinum.

In one embodiment, the closure element can be made at least in part of a high strength, low modulus metal alloy comprising Niobium, Tantalum, and at least one element selected from the group consisting of Zirconium, Tungsten, and Molybdenum. The closure element according to the present invention provide superior characteristics with regard to bio-compatibility, radio-opacity and MRI compatibility.

In one embodiment, the closure element can be made from or be coated with a biocompatible polymer. Examples of such biocompatible polymeric materials can include hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, polyp-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

V. Locator Assembly

Figure 13A:
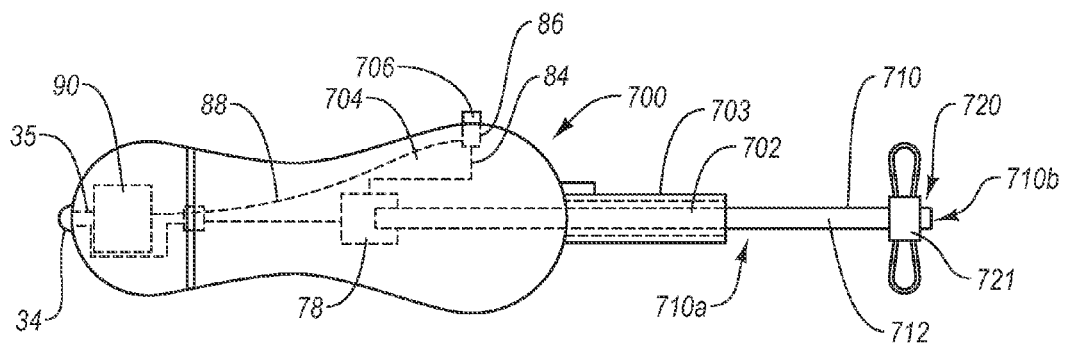
FIGS. 13A-13C illustrate an embodiment of a vessel closure device having a locator assembly that is configured for being deployed from the distal end of the vessel closure device through the opening so as to contact the internal surface of the blood vessel being repaired.

As shown in FIG. 13A, the vessel closure device 700 can include a locator (or obturator) assembly 712 that can be disposed within an internal lumen of the sheath 703, drive shaft 702, and/or carrier tube, which are described herein. The handle 704 can be configured with a button pad 706 that can actuate the locator assembly 712. Information related to vessel closure devices, locator assemblies, closure elements, closure element carrier assemblies, components thereof, mechanics thereof, and operation thereof can be obtained from U.S. Pat. No. 6,197,042 and co-pending applications and Ser. Nos. 09/610,128, 09/732,835, 09/866,551, 10/006, 400, 10/081,723, 10/356,214, 10/638,115, 11/048,503, 11/396,731, 11/744,089, 12/113,092, 60/946,042, and 60/946,030, the disclosures of which are expressly incorporated herein by reference.

The handle 704 can be configured and contain components as described in any of the preceding figures, such as FIGS. 1A-1B. The illustrated motor 78 can be more than one motor, where the different motors can operate different components of the device. For example, one motor 78 can operate the elongate drive member as described herein, and a second motor 78 can be operably coupled to the locator assembly 712. As such, the motor 78 can deploy the locator assembly 712, and then retract the locator assembly 712 as the closure element is being deployed. Also, the timing of retracting the locator assembly 712 to cooperate with deployment of the closure element for effective closing of the opening in the body lumen.

Being configured to extend into an opening in a blood vessel, the locator assembly 712 can selectably contact tissue within the blood vessel or adjacent to the opening. Whereby, the locator assembly 712 can be configured to draw the vessel closure device 700 taut and maintain the proper position of the device 700 in relation to the opening in the blood vessel. The locator assembly 712 can include a tubular body 710. As illustrated in FIG. 13A, the locator tubular body 710 has a proximal end region 710a and a distal end region 710b and includes a predetermined length and a predetermined outer cross-section, both of which can be of any suitable dimension. The distal end region 710b of the locator assembly 712 can include a substantially rounded, soft, and/or flexible distal end or tip 720 (e.g., locator) to facilitate atraumatic advancement and/or retraction of the flexible distal end region 710b through the opening and into the blood vessel.

Figure 13B:
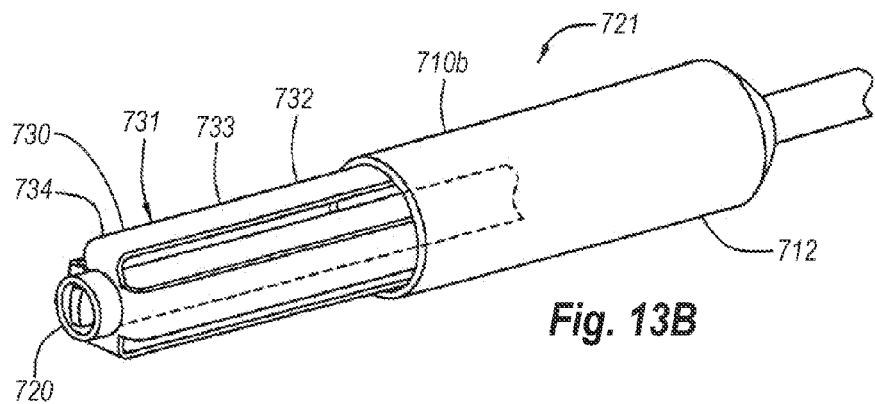
Figure 13C:
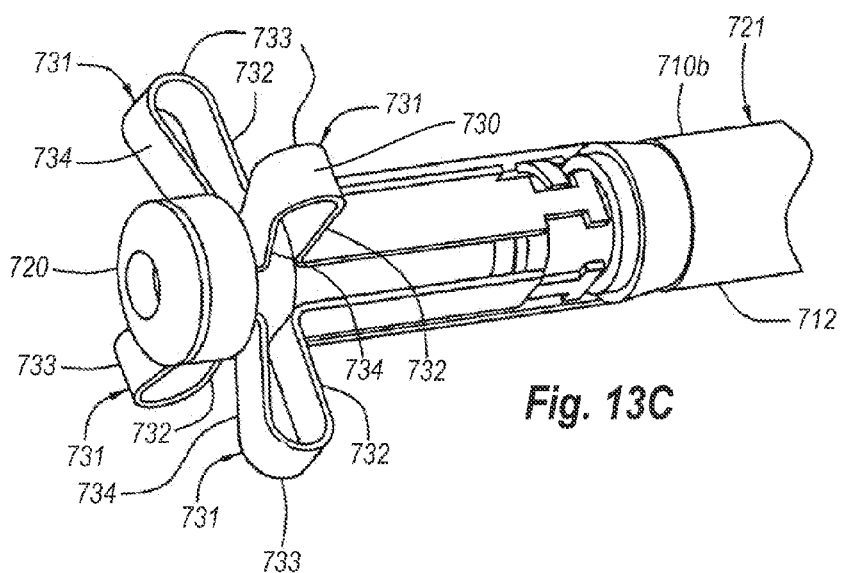

The locator 721 of the locator assembly 712 further can be selectably controllable between an unexpanded state (FIG. 13B) and an expanded state (FIG. 13C). In the unexpanded state, the locator 721 has an unexpanded size; whereas, the locator 721 in the expanded state has an expanded size, which is greater than the unexpanded size. The locator 721 can be configured to expand from the unexpanded size to the expanded size and/or to contract from the expanded size to the unexpanded size, and the expansion and contraction of the locator can be substantially uniform about a longitudinal axis of the locator assembly 712. For example, one or more expansion elements 730 (i.e., locator wings 730) can be provided on the locator 721, and can be configured to expand substantially transversely with respect to a longitudinal axis of the locator assembly 700. The expansion elements 730 can be substantially equally distributed about an outer periphery of the locator 721. Optionally, the expansion elements 730 may include radiopaque markers (not shown) or may be wholly or partially formed from a radiopaque material to facilitate observation of the expansion elements 730 and/or the locator 721 using fluoroscopy or other imaging systems.

At least one of the expansion elements 730 can include a substantially flexible member 731 with a substantially fixed end region 732, an intermediate region 733, and a movable end region 734 as shown in FIGS. 13B-13C. For each substantially flexible member 731, the fixed end region 732 can be fixedly coupled with the locator 720; whereas, the movable end region 734 can be movably coupled with the locator 720, and configured to be axially movable relative to the fixed end region 732. When each movable end region 734 can be axially moved toward the relevant fixed end region 732, the intermediate regions 733 buckle and/or expand transversely outwardly, thereby transitioning the locator 720 of the locator assembly 712 from the unexpanded state to the expanded state. In contrast, the locator 720 transitions from the expanded state to the unexpanded state as each of the movable end regions 734 are axially moved away from the relevant fixed end region 732. Although the expansion elements 730 are shown as including the flexible members 731 in FIGS. 13B-13C for purposes of illustration, it is understood that the expansion elements 730 can include any type of expansion elements and are not limited to the illustrated embodiments. It is further contemplated that the expansion elements 730 may further include geometric features that allow/enhance the ability of the expansion elements to bend or fold from a refracted position to an expanded position. The expansion elements 730 may be constructed of a material such as steel, spring steel, plastics or composites. In one embodiment, the expansion elements are constructed of nitinol.

During deployment, actuation of the button pad 706 can initiate deployment of a closure element. Prior to deployment, during deployment, or after deployment of the closure element, the locator 721 is withdrawn from the body lumen. The closure device may include a pad 706 with multiple actuators that allow an operator to separately control the actuation of the location and the actuation of the closure element deployment.

As discussed herein, the deployment of the closure element can be motor driven, pneumatically driven, or the like. Embodiments of the invention further contemplate manual deployment of the closure element. Embodiments of the invention provide a smooth deployment of the closure element. A motor driven (or other actuating mechanism) deployment can smoothly deploy the closure element in a manner that allows the closure element to engage the blood vessel (or other tissue) and then close the hole or opening in the blood vessel in a fluid and smooth motion.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference.

The invention claimed is:

1. A power driven vessel closure system for closing a hole in a wall of a body lumen, the vessel closure system comprising:
 a handle comprising:
  a power operated drive system; and
 one or more sheaths, each sheath including:
  a proximal end being removably couplable with the handle;
  an elongate drive member having a proximal end that is removably and operably couplable with the power operated drive system;
  a closure element removably and operably coupled with the elongate drive member, said closure element being retained in the sheath in a storage orientation; and
  a drive collar operatively coupled with the elongate drive member and the closure element, the drive collar being movable along a longitudinal axis of the elongate drive member and including a pusher surface configured to push the closure element within the sheath, and when said elongate drive member is operably coupled to the power operated drive system said elongate drive member is capable of distally moving the drive collar and the closure element within the sheath to a distal end of the elongate drive member and releasing the closure element from the vessel closure system into the wall of the body lumen so as to convert the closure element to a closed orientation and close the hole wherein the closure element is resilient from an open form in the storage orientation to a closed form in the closed orientation when released from the vessel closure system.

2. A vessel closure system as in claim 1, further comprising at least one of the following:
 one or more buttons disposed on the handle configured for manual actuation, wherein manual actuation of the button is capable of causing the power operated drive system to deliver the closure element into the wall of the body lumen so that the closure element converts to the closed orientation and closes the hole in the wall of the body lumen;
 one or more power sources, each including at least one of a power converter electronically couplable to an external power supply, a battery, a rechargeable battery, or a pressurized fluid chamber;
 one or more mechanical drive systems associated with or part of the power operated drive system, each including at least one of a motor, a transmission, gearing, a worm gear, a servomotor, a biased member having potential energy, a pump, a pressurized fluid chamber, or a pressurized hydraulic chamber;
 at least one of a worm drive system, a plunger, a shaft, a hollow tube, a threaded shaft, or a telescoping shaft; or
 one or more protective devices, each having an internal chamber configured to receive the handle such that the elongate drive member extends out from the internal chamber.

3. A vessel closure system as in claim 2, wherein the handle is comprised of a primary handle portion and a secondary handle portion that are removably couplable together so as to be fluid tight when coupled together, said primary handle portion being distally oriented during use and containing the power operated drive system and being configured to removably receive the proximal ends of the sheath and elongate drive member, and the secondary handle portion containing the power source.

4. A vessel closure system as in claim 1, wherein each sheath includes a lumen having at least a portion of the elongate drive member, a drive collar, and the closure element, said elongate drive member being operably coupled with the drive collar which is associated with the closure element, said sheath having a distal end that is configured to release the closure element from the drive collar and into the wall of the body lumen.

5. A vessel closure system as in claim 1, wherein the sheath is disposable.

6. A power driven vessel closure system for closing a hole in a wall of a body lumen, the vessel closure system comprising:
- a power source;
- a driver system operably couplable with the power source;
- an elongate drive member removably and operably couplable to the driver system;
- a drive collar operably coupled to the elongate drive member and movable relative to the elongate drive member; and
- a closure element associated with a surface of the drive collar configured to distally push the closure element, said closure element being retained in the vessel closure system in a deployment orientation and being capable of converting to a closed orientation when released from the vessel closure system into the wall of a body lumen so as to close the hole wherein the closure element is resilient from an open form in the deployment orientation to a closed form in the closed orientation when released from the vessel closure system.

7. A vessel closure system as in claim 6, further comprising at least one of the following:
- one or more buttons configured for manual actuation, wherein manual actuation of the button is capable of causing the driver system to activate the elongate drive member so as to operate the elongate drive member and translocate the drive collar from a deployment position to a terminal position, when in the terminal position the drive collar releases the closure element into the wall of the body lumen so that the closure element converts to the closed orientation and closes the hole in the wall of the body lumen;
- at least one of a power converter electronically couplable to an external power supply, a battery, a rechargeable battery, or a pressurized fluid chamber;
- at least one of a motor, a transmission, gearing, a worm gear, a servomotor, a biased member having potential energy, a pump, a pressurized fluid chamber, or a pressurized hydraulic chamber;
- at least one of a worm drive system, a plunger, a shaft, a hollow tube, a threaded shaft, or a telescoping shaft;
- one or more protective devices for the vessel closure system; or
- one or more sheaths each having a sheath lumen containing at least a portion of the elongate drive member, the drive collar, and the closure element, said sheath having a proximal end that is removably couplable to a housing that contains the power source and driver system, and having a distal end that is configured to release the closure element into the wall of the body lumen, wherein at least one of the one or more sheaths is disposable or reusable.

8. A vessel closure system as in claim 7, further comprising:
- a handle containing the:
  - the power source;
  - the driver system; and
  - a proximal end of the elongate drive member such that the elongate drive member is operably coupled to the driver system.

9. A vessel closure system as in claim 8, wherein the handle is comprised of a primary handle portion and a secondary handle portion that are removably couplable together so as to be fluid tight when coupled together, and the primary handle portion contains the driver system and is configured to receive the proximal ends of the sheath and elongate drive member, and the secondary handle portion contains the power source.

10. A vessel closure system as in claim 9, wherein the one or more protective devices is included and has an internal chamber that is configured to receive the handle and the proximal end of the elongate drive member such that a distal end of the elongate drive member extends out from the internal chamber, said protective device includes an openable sealing mechanism that is configured to open to receive the handle and to close and provide a fluid-tight seal, and includes an aperture opposite of the openable sealing mechanism, said aperture configured to receive the proximal end of the sheath therethrough so as to provide a fluid-tight seal with the sheath with a distal end of the sheath extending from the protective device, said sheath containing the elongate drive member, drive collar, and closure element.

11. A kit comprising:
- a power driven vessel closure system for closing a hole in a wall of a body lumen, the vessel closure system comprising:
  - a fluid-tight modular handle comprising:
    - a power source; and
    - a power operated drive system operably coupled with the power source; and
  - a plurality of disposable sheaths, each sheath having a proximal end being removably couplable with the handle, each sheath comprising:
    - an elongate drive member having a proximal end that is removably and operably couplable with the power operated drive system;
    - a closure element removably and operably coupled with the elongate drive member, said closure element being retained in the sheath in a storage orientation, and when said elongate drive member is operably coupled to the power operated drive system said elongate drive member is capable of distally moving the closure element within the sheath to the distal end of the elongate drive member and releasing the closure element from the elongate drive member and sheath into the wall of the body lumen so as to convert the closure element to a closed orientation and close the hole, wherein the closure element is resilient from an open form in the storage orientation to a closed form in the closed orientation when released from the vessel closure system; and
    - a drive collar operatively coupled with the elongate drive member and the closure element, the drive collar being movable relative to the elongate drive member and including a pusher surface configured to push the closure element and to hold the closure element away from the sheath.

12. A kit as in claim 11, further comprising a plurality of disposable protective devices configured to protect the handle.

* * * * *